(12) United States Patent
Browne et al.

(10) Patent No.: US 11,730,356 B2
(45) Date of Patent: Aug. 22, 2023

(54) MOBILE OPHTHALMIC DEVICE

(71) Applicant: Vision Products, LLC, Campbell, CA (US)

(72) Inventors: Michael P. Browne, San Mateo, CA (US); Andrew J. Olson, San Jose, CA (US); Nathan J. Fo, Fremont, CA (US)

(73) Assignee: Vision Products, LLC, Campbell, CA (US)

( * ) Notice: Subject to any disclaimer, the term of this patent is extended or adjusted under 35 U.S.C. 154(b) by 200 days.

(21) Appl. No.: 15/806,279

(22) Filed: Nov. 7, 2017

(65) Prior Publication Data

US 2019/0133435 A1 May 9, 2019

Related U.S. Application Data

(60) Provisional application No. 62/582,299, filed on Nov. 6, 2017.

(51) Int. Cl.
*A61B 3/00* (2006.01)
*A61B 3/135* (2006.01)
(Continued)

(52) U.S. Cl.
CPC ............ *A61B 3/005* (2013.01); *A61B 3/0008* (2013.01); *A61B 3/0083* (2013.01); *A61B 3/112* (2013.01);
(Continued)

(58) Field of Classification Search
CPC A61B 3/14; A61B 3/112; A61B 3/117; A61B 3/135; A61B 3/145; A61B 3/18; A61B 3/12; A61B 3/1208; A61B 3/10; A61B 3/0008; A61B 3/0083; A61B 3/005; A61B 5/0013; A61B 5/0077;
(Continued)

(56) References Cited

U.S. PATENT DOCUMENTS 4,411,502 A * 10/1983 Lang .................. A61B 3/135
351/221
5,442,489 A 8/1995 Yamamoto et al.
(Continued)

FOREIGN PATENT DOCUMENTS

CN 203555720 U 4/2014
WO WO 2015/049404 A1 4/2015
WO WO 2016/179370 A1 11/2016

OTHER PUBLICATIONS

Welch Allyn PanOptic™ Ophthalmoscope Overview, https://diagnosis101.welchallyn.com/ophthalmoscopy/panoptic/, Captured Apr. 27, 2019.
(Continued)

*Primary Examiner* — Nicholas R. Pasko
(74) *Attorney, Agent, or Firm* — Knobbe, Martens, Olson & Bear, LLP

(57) ABSTRACT

A handheld ophthalmic device configured to perform various optical diagnostic tests to determine the health of a subject's eye. The handheld ophthalmic device is configured to be attached to a smartphone, a cell phone or an electronic tablet. The smartphone, a cell phone or an electronic tablet can be used to view images obtained by the handheld ophthalmic device and to transmit data and images obtained by the handheld ophthalmic device to an ophthalmologist located remotely.

44 Claims, 5 Drawing Sheets

(51) Int. Cl.
  *A61B 3/14* (2006.01)
  *A61B 5/00* (2006.01)
  *A61B 3/11* (2006.01)
  *A61B 3/18* (2006.01)
  *A61B 3/117* (2006.01)

(52) U.S. Cl.
  CPC .............. *A61B 3/117* (2013.01); *A61B 3/135* (2013.01); *A61B 3/14* (2013.01); *A61B 3/145* (2013.01); *A61B 3/18* (2013.01); *A61B 5/0013* (2013.01); *A61B 5/0077* (2013.01); *A61B 5/6898* (2013.01); *A61B 2560/0431* (2013.01); *A61B 2560/0456* (2013.01); *A61B 2560/0475* (2013.01)

(58) Field of Classification Search
  CPC .......... A61B 5/6898; A61B 2560/0431; A61B 2560/0456; A61B 2560/0475; A61B 1/0684; A61B 2090/309; A61B 2576/00; A61B 3/00; H04N 5/2256; H04M 1/72527; H04M 2250/52; H04M 1/0264; H04M 1/04; G02B 13/001; G06F 1/1632; G06F 19/3418; G06F 1/1626; G06T 2207/30041; G06T 7/0012
  USPC ............... 351/206, 208, 214; 348/78, 207.1; 362/3; 396/544; 455/41.2
  See application file for complete search history.

(56) References Cited

U.S. PATENT DOCUMENTS

| | | |
|---|---|---|
| 7,883,210 B2 | 2/2011 | Filar |
| 8,262,221 B2 | 9/2012 | Filar |
| 8,944,596 B2 | 2/2015 | Wood et al. |
| 9,706,918 B2 | 7/2017 | Myung et al. |
| 10,028,649 B2 | 7/2018 | Salvati et al. |
| 2012/0287402 A1 | 11/2012 | Davis |
| 2012/0320340 A1 | 12/2012 | Coleman, III |
| 2013/0083185 A1 | 4/2013 | Coleman, III |
| 2016/0051142 A1 | 2/2016 | Howes |
| 2016/0073878 A1* | 3/2016 | Su .................. A61B 3/0025 351/246 |
| 2016/0249804 A1 | 9/2016 | Wang |
| 2018/0055357 A1* | 3/2018 | Meyerson ............ A61B 3/14 |
| 2018/0153399 A1* | 6/2018 | Fink .................... A61B 3/0008 |

OTHER PUBLICATIONS

Welch Allyn PanOptic™ Ophthalmoscope (2008), https://pdf.medicalexpo.com/pdf/welch-allyn-panoptic-ophthalmoscope/70854-82485-_2.html, downloaded Jul. 1, 2020.

Department of Defense. (2012-2013). Army: 30 Phase I Selections from the 12.3 Solicitation. Retrieved from http://www.dodsbir.net/selections/abs2012-3/dodabs123.htm (80 pages).

Food and Drug Administration. (Jul. 8, 1998). *Guidance for Industry: Slit Lamp Guidance.* Retrieved from Food and Drug Administration. (Jul. 8, 1998). *Guidance for Industry: Ophthalmoscope Guidance—(Direct and Indirect).* Retrieved from http://www.fda.gov/MedicalDevices/DeviceRegulationandGuidance/GuidanceDocuments/ucm080174.htm (10 pages)

Food and Drug Administration (Dec. 20, 2012). Welch Allyn: 510(k). Retrieved from http://www.accessdata.fda.gov/cdrh_docs/pdf12/K121405.pdf (12 pages).

Food and Drug Administration. (Sep. 25, 2013). *Mobile Medical Applications: Guidance for Industry and Food and Drug Administration Staff.* Retrieved from: http://www.fda.gov/downloads/MedicalDevices/DeviceRegulationandGuidance/GuidanceDocuments/UCM263366.pdf (44 pages).

Myung, D., Jais, A., He L., and Chang R.T. (2014b). 3D Printed Smartphone Indirect Lens Adapter for Rapid, High Quality Retinal Imaging. *Journal MTM,* 3:1:9-15. Retrieved from http://www.journalmtm.com/2014/3d-prited-smartphone-indirect-lens-adapter-for-rapid-high-quality-retinal-imaging/ (12 pages).

Slonim, C. (Sep. 10, 2010). What should be done to erasure that non-ophthalmologist medical personnel are properly trained to recognize and treat ocular traumatic injuries? How much treatment should they administer? *Ocular Surgery News.* Retrieved from: http://www.healio.com/ophthalmology/oculoplastics/news/print/ocula-surgery-news/%7B87903399-9849-4cb2-9f9c-0c3073ca6c2b%70/what-should-be-done-to-ensure-that-non-ophthalmologist-medical-peresonnel-are-properly-trained-to-recognize-and-treat-ocular-traumatic-injuries-how-much-treatment-should-they-administer (2 pages).

Spector, R. (Mar. 7, 2014). Smartphones become 'eye-phones' with low-cost devices developed by ophthalmologists. *Stanford Medicine News Center.* Retrieved from http://med.stanford.edu/news/all-news/2014/03/smartphones-become-eye-phones-with-low-cost-devices-developed-by-ophthalmologists.html (4 pages).

VisionAware.org. (n.d.b.). Statistics on Vision Loss and the Military and Policy Implications. Retrieved from http://www.visionaware.org/info/everyday-living/essential-skills/information-for-veterans-coping-with-vision-loss/statistics-on-vision-loss-and-the-military/1235 (4 pages).

Wilson, J. (Dec. 16, 2012). *Combat Eye Trauma.* Retrieved from http://www.devensemedianetwork.com/stories/combat-eye-trauma/ (6 pages).

* cited by examiner

MOBILE OPHTHALMIC DEVICE

CROSS-REFERENCE TO RELATED APPLICATIONS

This application claims the benefit of priority under 35 U.S.C. § 119(e) of U.S. Provisional Patent Application No. 62/582,299, filed on Nov. 6, 2017 and titled "MOBILE OPHTHALMIC DEVICE," which is hereby incorporated by reference herein in its entirety for all purposes.

STATEMENT REGARDING FEDERALLY SPONSORED R&D

This invention was made with government support under Contract No. W81XWH-13-C-0115 awarded by the United States Army. The government has certain rights in the invention.

BACKGROUND

Field

This application generally relates to the field of ophthalmic devices used for examination of a human eye.

Description of the Related Technology

Ophthalmologists and optometrists use various optical diagnostic instruments to assess, diagnose, and treat ailments and injuries of the eye. Such optical diagnostic instruments can be heavy and bulky or at least not convenient to carry around. Furthermore, most ophthalmic diagnostic instruments are configured for use in a hospital or a clinical setting and maybe less suitable for use in a battlefield, disaster area or other austere environments where there may be need for such diagnostic instruments. Additionally, an ophthalmologist or an optometrist may not be available on the battlefield or the particular site of the injury or injured. Accordingly, there is a need for compact optical diagnostic instruments that are capable of transmitting measurements, images and/or data obtained by the optical diagnostic instruments to an ophthalmologist or an optometrist for a remote consultation.

SUMMARY

Various systems and methods discussed herein are accordingly directed towards a handheld ophthalmic device that is sufficiently light weight and compact to be carried on the battlefield by a soldier, a medic, or other civilian or military personnel. The device is also sufficiently small and light weight so as to be held in the hand in front of the face of a person with an eye injury, for example, to obtain one or more images of the injured eye. The handheld ophthalmic device is configured to be attached to the rear of a mobile communication device, such as, for example, a smartphone, a cell phone or an electronic tablet. Such mobile communication devices, e.g., a smart phone, a cell phone or an electronic tablet, are generally configured to communicate over a distance greater than about 100-120 feet, such as, for example, greater than or equal to 1000 feet, 5000 feet, a mile, 2 miles or more using cellular technology. Accordingly, the handheld ophthalmic device can be configured to mate with mobile communications devices that comprise transmitters and receivers that are configured to wirelessly communicate over a distance greater than about 100-120 feet, greater than 1000 feet, 5000 feet, a mile, 2 miles or more. In particular, in various implementations, the handheld ophthalmic device can comprise a mechanical docking system that is configured to receive the mobile communication device, such as, for example, a smartphone, a cell phone or an electronic tablet. The docking system can be removably attached to the handheld ophthalmic device. In some implementations, an appropriate docking system that is sized to match the size of the operator's smart phone, cell phone or electronic tablet can be attached to the handheld ophthalmic device.

The handheld ophthalmic device can comprise one or more cameras or imaging systems and/or one or more illumination sources that are configured to image and/or otherwise facilitate examination of the eye and/or the face of a subject proximal to the eye. The handheld ophthalmic device allows an operator to capture images of an eye and/or face of a subject and remotely share the captured images with eye care professionals using telecommunications. Various implementations of the handheld ophthalmic device may, for example, comprise a combination of an ophthalmoscope configured to examine the retina, fundus and/or other internal structures of a subject's eye, and a slit-lamp to examine the subject's cornea, iris, lens, conjunctiva, and/or eyelids. Accordingly, some implementations of the handheld ophthalmic device can comprise: (i) a first camera and a first source of illumination that is configured as an ophthalmoscope configured to examine the retina or fundus of a subject's eye; and (ii) at least a second camera and/or a second illumination source that is configured to perform a slit-lamp examination of a subject's eye. Various implementations of the handheld ophthalmic device can further comprise a near-infrared (NIR) camera, a near-infrared illuminator and/or a source of white light that can be used to perform pupillography and/or obtain images of the subject's eyes and/or face.

Another implementation of a handheld ophthalmic device disclosed herein can comprise an ophthalmoscope configured to examine the fundus, retina, and/or internal structures of a subject's eye and a stand comprising a slit-lamp to which the handheld ophthalmic device can be attached. In some implementations, the stand can further comprise a chin rest.

The images (e.g., still or video) obtained by the one or more cameras of the handheld ophthalmic device can be transported to the mobile communication device, such as, for example, smart phone, cell phone or electronic tablet to be displayed on a display device (e.g., a touch sensitive screen) incorporated in the mobile communication device, stored in a memory of the mobile communication device and/or transmitted to a doctor or a healthcare professional for review.

Accordingly, the handheld ophthalmic device can provide a portable telemedicine platform that can allows operators such as soldiers, medics, or other military or civilian personnel to capture images and data of a subject's eye and/or face, make assessments regarding the health of the subject based on the captured images and data and/or share the captured images and data with ophthalmologists or other medical personnel located remotely from the subject and the operator. It is contemplated that in some cases, a software application ("app") executed by an electronic processing system (e.g., electronic processing system of the mobile communication device (e.g., smartphone or cell phone), the electronics of the handheld ophthalmic device or a combination of the electronic processing system of the mobile communication device and the electronics of the handheld ophthalmic device) can guide operators in properly capturing images of the subject's eye and/or face and/or in making assessments regarding the health of the subject based on the captured images and data. For example, the software application can guide the operator regarding proper placement of the handheld ophthalmic device with respect to the subject's eye for a funduscopic examination, a slit lamp examination or a near infrared pupillography examination.

It is contemplated that the handheld ophthalmic device is configured for use in austere or remote environments (e.g., battle fields, disaster areas, remote rugged locations, etc.). The images of the eye and/or face of a subject proximal to the eye captured by the handheld ophthalmic device can be transmitted to a physician, an ophthalmologist, an optometrist, or other health care provider to detect and evaluate injuries to the eye and/or face and provide telemedicine services to the subject experiencing eye trauma and/or injuries. It is further contemplated that the captured images can be stored, in case it is not possible to transmit them to the ophthalmologist/optometrist, etc., until mobile/cellular communication is available.

The handheld ophthalmic device can be used by firefighters, rescue workers, emergency personnel, first responders, etc. at the site of an accident, disaster, or otherwise in the field that may have limited access to an ophthalmologist or physician. The images of the patient's eye and/or face can be transmitted to an ophthalmologist or other health care professional at a different location for possible assessment, diagnosis and/or treatment.

The handheld ophthalmic device can also be used in rural hospitals, community hospitals and/or emergency departments that may have limited access to an ophthalmologist or particular specialist. The images of the patient's eye and/or face obtained at a rural hospital, community hospital and/or emergency department can be transmitted to an ophthalmologist or specialist at a different location for possible assessment, diagnosis, treatment and/or support.

Various examples of ophthalmic devices and their methods of use are described herein such as the examples enumerated below:

Example 1: A handheld ophthalmic device comprising:
a mechanical assembly comprising:
a first camera and a first source of illumination configured as an ophthalmoscope;
a second source of illumination configured to be laterally translated; at least a second camera, wherein the second source of illumination and at least the second camera are configured as a slit lamp;
electronics; and
a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the smartphone, the cellphone or the electronic tablet is disposed on a rear side of the mechanical assembly opposite a front side of the mechanical assembly through which the ophthalmoscope and the slit lamp are configured to emit and capture light,
wherein the handheld ophthalmic device is configured to be operated in a first mode as an opthalmoscope and in a second mode as a slit-lamp to examine an eye of a subject facing the front side of the mechanical assembly, and
wherein the electronics are configured to electronically communicate with the smartphone, the cellphone or the electronic tablet and transport one or more images captured by the first camera in the first mode or at least the second camera in the second mode to the smartphone, the cellphone or the electronic tablet.

Example 2: The handheld ophthalmic device of Example 1, further comprising the smartphone, the cellphone or the electronic tablet, wherein the smartphone, the cellphone or the electronic tablet comprises a software application which when executed by an electronic processing system guides an operator to capture the one or more images.

Example 3: The handheld ophthalmic device of any of Examples 1-2, further comprising the smartphone, the cellphone or the electronic tablet, wherein the smartphone, the cellphone or the electronic tablet comprises a software application which when executed by an electronic processing system guides an operator to perform an assessment based on the captured one or more images.

Example 4: The handheld ophthalmic device of any of Examples 1-3, further comprising the smartphone, the cellphone or the electronic tablet, wherein the one or more images captured by the first or at least the second camera are stored in the memory device of the smartphone, the cellphone or the electronic tablet.

Example 5: The handheld ophthalmic device of any of Examples 1-4, further comprising the smartphone, the cellphone or the electronic tablet, wherein the smartphone, the cellphone or the electronic tablet comprises instructions which when executed by an electronic processing system causes the smartphone, the cellphone or the electronic tablet to transport the one or more images captured by the first or at least the second camera to an ophthalmologist, an optometrist or an expert at a remote location.

Example 6: The handheld ophthalmic device of any of Examples 1-5, further comprising the smartphone, the cellphone or the electronic tablet, wherein the smartphone, the cellphone or the electronic tablet comprises instructions which when executed by an electronic processing system causes the smartphone, the cellphone or the electronic tablet to display the one or more images captured by the first or at least the second camera on the display device of the smartphone, the cellphone or the electronic tablet.

Example 7: The handheld ophthalmic device of any of Examples 1-6, further comprising the smartphone, the cellphone or the electronic tablet, wherein the electronics is configured to electronically communicate with the smartphone, the cellphone or the electronic tablet.

Example 8: The handheld ophthalmic device of any of Examples 1-7, further comprising the smartphone, the cellphone or the electronic tablet, wherein an electronic processing system of the smartphone is configured to obtain instructions stored in a non-transitory storage medium, and
wherein the obtained instructions when executed by an electronic processing system cause the smartphone, the cellphone or the electronic tablet to:
guide an operator to capture the one or more images,
guide an operator to perform an assessment based on the captured one or more images,
display the captured one or more images, or
transmit the captured one or more images to a healthcare professional, an ophthalmologist, doctor or an optometrist.

Example 9: The handheld ophthalmic device of any of Examples 1-8, wherein the electronics comprises a transmitter and a receiver.

Example 10: The handheld ophthalmic device of any Example 1-9, wherein the electronics comprises a wireless transmitter and a wireless receiver.

Example 11: The handheld ophthalmic device of any of Examples 1-10, further comprising a third camera and a third source of illumination configured as a near infrared pupillography instrument.

Example 12: The handheld ophthalmic device of Example 11, wherein the third source of illumination is configured to emit near infrared light in a wavelength range between 700 nm and 1100 nm or white light.

Example 13: The handheld ophthalmic device of any of Examples 11-12, wherein the third camera is configured to receive and detect near infrared light.

Example 14: The handheld ophthalmic device of any of Examples 11-13, wherein the third camera is configured to obtain a video of pupillary reaction of the subject's eye when illuminated by light in a wavelength range between about 700 nm and about 1100 nm.

Example 15: The handheld ophthalmic device of any of Examples 11-14, further comprising a fourth source configured to emit white light or near infrared light in a wavelength range between 700 nm and 1100 nm.

Example 16: The handheld ophthalmic device of any of Examples 11-15, wherein the third camera is configured to obtain an image of the subject's eye or face when illuminated by white light.

Example 17: The handheld ophthalmic device of any of Examples 1-16, further comprising a stand configured to hold the mechanical assembly.

Example 18: The handheld ophthalmic device of Example 17, wherein the stand is portable.

Example 19: The handheld ophthalmic device of any of Examples 17-18, wherein the stand comprises a chinrest.

Example 20: The handheld ophthalmic device of any of Examples 17-19, wherein the stand comprises a secondary slit-lamp.

Example 21: The handheld ophthalmic device of any of Examples 1-20, wherein the first camera and the first source of illumination are disposed in a hinged compartment.

Example 22: The handheld ophthalmic device of any of Examples 1-21, wherein the second source of illumination is disposed in a housing.

Example 23: The handheld ophthalmic device of any of Examples 1-22, wherein the second source of illumination is disposed in a housing attached to one or more tracks on a portion of the front side of the mechanical assembly.

Example 24: The handheld ophthalmic device of Example 23, wherein the portion of the front side of the mechanical assembly comprising the one or more tracks is curved.

Example 25: A handheld ophthalmic device comprising: a mechanical assembly comprising:
  a mobile slit-lamp configured to be laterally translated, the mobile slit-lamp comprising a light source;
  an imaging system;
  electronics; and
  a docking system configured to receive and hold a smartphone, a cellphone or a electronic tablet, wherein the smartphone, the cellphone or the electronic tablet comprises a display device, a memory device, and a mobile communication system configured to communicate over a distance greater than about 1000 feet, wherein the smartphone, the cellphone or the electronic tablet is disposed on a rear side of the mechanical assembly opposite a front side of the mechanical assembly through which the mobile slit lamp is configured to emit and capture light,
  wherein the electronics is configured to transport one or more images captured by the imaging system to the smartphone, the cellphone or the electronic tablet.

Example 26: The handheld ophthalmic device of Example 25, wherein the assembly further comprises:
  a second camera; and
  a second optical source,
  wherein the second camera is configured to obtain one or more images of the subject's eye when illuminated by light from the second optical source, and
  wherein the one or more images obtained by the second camera are transported via the electronics to the smartphone, the cellphone or the electronic tablet.

Example 27: The handheld ophthalmic device of any of Examples 25-26, wherein the assembly further comprises:
  a third camera and a third source of illumination configured as a near infrared pupillography instrument or a facial imaging system,
  wherein the third source of illumination is configured to emit white light or near infrared light in a wavelength range between 700 nm and 1100 nm, and
  wherein the third camera is configured to receive and detect white light or near infrared light.

Example 28: The handheld ophthalmic device of Example 27, wherein the third camera is configured to obtain a video of pupillary reaction of a subject's eye when illuminated by light from the third source of illumination.

Example 29: The handheld ophthalmic device of any of Examples 27-28, further comprising a fourth source of illumination configured to emit white light or near infrared light in a wavelength range between 700 nm and 1100 nm.

Example 30: The handheld ophthalmic device of Example 29, wherein the third camera is configured to obtain an image of an subject's eye or face when illuminated by white light.

Example 31: The handheld ophthalmic device of any of Examples 25-30, further comprising a stand configured to hold the mechanical assembly.

Example 32: The handheld ophthalmic device of Example 31, wherein the stand is portable.

Example 33: The handheld ophthalmic device of any of Examples 31-32, wherein the stand comprises a chinrest.

Example 34: The handheld ophthalmic device of any Example 31-33, wherein the stand comprises a secondary slit-lamp.

Example 35: A handheld ophthalmic device comprising:
  a mechanical assembly comprising:
    a first camera and a first source of illumination configured as an ophthalmoscope;
    a second source of illumination, the second source of illumination configured to emit white light or light in a wavelength range between about 700 nm and about 1100 nm;
    a second camera configured to receive and detect light in a wavelength range between about 700 nm and about 1100 nm;
    electronics; and
    a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the smartphone, the cellphone or the electronic tablet is disposed on a rear side of the mechanical assembly opposite a front side of the mechanical assembly through which the first and the second source of illumination are configured to emit light, wherein the electronics is configured to transport one or more images captured by the first or the second camera to the smartphone, the cellphone or the electronic tablet.

Example 36: The handheld ophthalmic device of Example 35, wherein the electronics comprises a transmitter and a receiver.

Example 37: The handheld ophthalmic device of any of Examples 35-36, wherein the electronics comprises a wireless transmitter and a wireless receiver.

Example 38: The handheld ophthalmic device of any of Examples 35-37, wherein the second camera is configured to obtain a video of pupillary reaction of a subject's eye when illuminated by light in a wavelength range between about 700 nm and about 1100 nm.

Example 39: The handheld ophthalmic device of any of Examples 35-38, further comprising a third source configured to emit white light or light in a wavelength range between about 700 nm and about 1100 nm.

Example 40: The handheld ophthalmic device of Example 39, wherein the second camera is configured to obtain an image of an subject's eye or face when illuminated by white light.

Example 41: The handheld ophthalmic device of any of Examples 35-40, further comprising a stand configured to hold the mechanical assembly.

Example 42: The handheld ophthalmic device of Example 41, wherein the stand is portable.

Example 43: The handheld ophthalmic device of any of Examples 41-42, wherein the stand comprises a chinrest.

Example 44: The handheld ophthalmic device of any of Examples 41-43, wherein the stand comprises a slit-lamp.

Example 45: The handheld ophthalmic device of any of Example 35-44, wherein the mechanical assembly comprises a fourth source of illumination configured to be laterally translated.

Example 46: The handheld ophthalmic device of Example 45, wherein the mechanical assembly comprises at least a fourth camera configured to image an eye of a subject illuminated by light from the fourth source of illumination.

Example 47: The handheld ophthalmic device of Example 46, wherein the fourth source of illumination and at least the fourth camera are configured as a slit lamp.

Example 48: The handheld ophthalmic device of any of Examples 45-47, wherein the fourth source of illumination is disposed in a housing attached to one or more tracks on a portion of the front side of the mechanical assembly.

Example 49: The handheld ophthalmic device of Example 48, wherein the one or more tracks of the portion of the front side of the mechanical assembly comprising the one or more tracks is curved.

Example 50: The handheld ophthalmic device of any of Examples 35-49, wherein the first camera and the first source of illumination are disposed in a hinged compartment.

Example 51: An ophthalmic device comprising:
a stand; and
a handheld mechanical assembly configured to be removably attached to the stand, wherein the handheld mechanical assembly comprises:
 a first camera and a first source of illumination configured as an ophthalmoscope;
 electronics; and
 a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the smartphone, the cellphone or the electronic tablet is disposed on a rear side of the mechanical assembly opposite a front side of the mechanical assembly through which the ophthalmoscope is configured to emit and capture light,
wherein the electronics is configured to transport one or more images captured by the first camera to the smartphone, the cellphone or the electronic tablet.

Example 52: The ophthalmic device of Example 51, wherein the wherein the stand is portable.

Example 53: The ophthalmic device of any of Examples 51-52, wherein the stand comprises a chinrest.

Example 54: The ophthalmic device of any of Examples 51-53, wherein the stand comprises a slit-lamp.

Example 55: The ophthalmic device of Example 54, wherein the stand comprises a movement assembly configured to translate the slit-lamp.

Example 56: The ophthalmic device of any of Examples 54-55, wherein the slit-lamp comprises:
 a second source of illumination configured to be laterally translated; and
 at least a second camera;

Example 57: The ophthalmic device of any of Examples 51-56, further comprising a third camera and a third source of illumination configured as a near infrared pupillography instrument or a facial imaging instrument.

Example 58: The ophthalmic device of Example 57, wherein the third source of illumination is configured to emit white light or near infrared light in a wavelength range between 700 nm and 1100 nm.

Example 59: The ophthalmic device of any of Examples 57-58, wherein the third camera is configured to receive and detect near infrared light.

Example 60: The ophthalmic device of any of Examples 57-59, wherein the third camera is configured to obtain a video of pupillary reaction of the subject's eye when illuminated by near infrared light.

Example 61: The ophthalmic device of any of Examples 57-60, further comprising a fourth source configured to emit white light or near infrared light.

Example 62: The ophthalmic device of any of Examples 57-61, wherein the third camera is configured to obtain an image of the subject's eye or face when illuminated by white light.

Example 63: An ophthalmic device comprising:
a stand; and
a handheld ophthalmic device configured to be removably attached to the stand, the handheld ophthalmic device comprising:
 a source of illumination configured to be laterally translated;
 electronics; and
 a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the smartphone, the cellphone or the electronic tablet is disposed on a rear side of the mechanical assembly opposite a front side of the mechanical assembly through which the source of illumination is configured to emit light, and wherein the electronics is configured to electronically communicate with the smartphone, the cellphone or the electronic tablet.

Example 64: The ophthalmic device of Example 63, wherein the wherein the stand is portable.

Example 65: The ophthalmic device of any Examples 63-64, wherein the stand comprises a chinrest.

Example 66: The ophthalmic device of any Examples 63-65, wherein the handheld ophthalmic device further comprises an imaging system configured to capture one or more images of a subject's eye when illuminated by light from the source of illumination.

Example 67: The ophthalmic device of Example 66, wherein the one or more images captured by the imaging system are transported via the electronics to the smartphone, the cellphone or the electronic tablet.

Example 68: A non-transitory storage medium comprising instructions which when executed by an electronic processing system causes a smartphone, a cellphone or an electronic tablet to establish electrical communication with electronics of a handheld ophthalmic device mechanically attached to the rear of the smartphone, the cellphone or the electronic tablet,
  wherein the handheld ophthalmic device comprises:
  at least one light source configured to illuminate a portion of an eye of a subject;
  at least one camera configured to capture an image of the illuminated portion of the eye of the subject;
  electronics configured to electronically communicate with the smartphone, the cellphone or the electronic tablet; and
  a docking station configured to receive and hold the smartphone, the cellphone or the electronic tablet.

Example 69: The non-transitory storage medium of Example 68, wherein the instructions when executed by the electronic processing system further causes the smartphone, the cellphone or the electronic tablet to guide an operator to capture the image of the subject's eye with the handheld ophthalmic device.

Example 70: The non-transitory storage medium of any Examples 68-69, wherein the instructions when executed by the electronic processing system further causes the smartphone, the cellphone or the electronic tablet to guide an operator to perform an assessment based on the captured image.

Example 71: The non-transitory storage medium of any Examples 68-70, wherein the instructions when executed by the electronic processing system further causes the smartphone, the cellphone or the electronic tablet to display the captured image on a display device of the smartphone, the cellphone or the electronic tablet.

Example 72: The non-transitory storage medium of any Examples 68-71, wherein the instructions when executed by the electronic processing system further causes the smartphone, the cellphone or the electronic tablet to store the captured image in a memory device of the smartphone, the cellphone or the electronic tablet.

Example 73: The non-transitory storage medium of any Examples 68-72, wherein the instructions when executed by the electronic processing system further causes the smartphone, the cellphone or the electronic tablet to transport the captured image to an ophthalmologist or an optometrist located remotely.

Example 74: The non-transitory storage medium of any Examples 68-73, wherein the instructions when executed by the electronic processing system further causes the smartphone, the cellphone or the electronic tablet to guide an operator to perform a pupillography examination.

Example 75: The non-transitory storage medium of any Examples 68-74, wherein the instructions when executed by the electronic processing system further causes the smartphone, the cellphone or the electronic tablet to guide an operator to perform a slit lamp examination.

Example 76: A method of performing an ophthalmic evaluation on a subject, the method comprising:
  (a) coupling a cell phone with an handheld ophthalmic device comprising:
    (i) at least one light source configured to illuminate a portion of an eye of a subject;
    (ii) at least one camera configured to capture an image of the illuminated portion of the eye of the subject;
    (iii) electronics configured to electronically communicate with the cellphone; and
    (iv) a docking station configured to receive and hold the cellphone; and
  (b) establishing electrical communication between the cell phone and the electronics of a handheld ophthalmic device mechanically attached to the rear of the cell phone.

Example 77: The method of Example 76, capturing an image of the subject's eye with the handheld ophthalmic device based on instructions from the cell phone.

Example 78: The method of Examples 76 or 77, further comprising performing an assessment based on the captured image based on instruction from the cell phone.

Example 79: The method of any of Examples 76 to 78, further comprising displaying the captured image on a display device of the cellphone.

Example 80: The method of any of Examples 76 to 79, further comprising storing the captured image in a memory device of the cellphone.

Example 81: The method of any of Examples 76 to 80, further comprising transporting the captured image to a doctor, a clinician, an ophthalmologist or an optometrist located remotely.

Example 82: The handheld ophthalmic device of any of Examples 1-24, wherein the docking system is configured to receive and hold the smartphone.

Example 83: The handheld ophthalmic device of any of Examples 1-24, wherein the docking system is configured to receive and hold the cell phone.

Example 84: The handheld ophthalmic device of any of Examples 25-34, wherein the docking system is configured to receive and hold the smartphone.

Example 85: The handheld ophthalmic device of any of Examples 25-34, wherein the docking system is configured to receive and hold the cell phone.

Example 86: The handheld ophthalmic device of any of Examples 35-50, wherein the docking system is configured to receive and hold the smartphone.

Example 87: The handheld ophthalmic device of any of Examples 35-50, wherein the docking system is configured to receive and hold the cell phone.

Example 88: The ophthalmic device of any of Examples 51-62, wherein the docking system is configured to receive and hold the smartphone.

Example 89: The ophthalmic device of any of Examples 51-62, wherein the docking system is configured to receive and hold the cell phone.

Example 90: The ophthalmic device of any of Examples 63-67, f wherein the docking system is configured to receive and hold the smartphone.

Example 91: The ophthalmic device of any of Examples 63-67, wherein the docking system is configured to receive and hold the cell phone.

Example 92: The non-transitory storage medium of any of Examples 68-75, wherein the docking system is configured to receive and hold the smartphone.

Example 93: The non-transitory storage medium of any of Examples 68-75, wherein the docking system is configured to receive and hold the cell phone.

Example 94: The method of any of Examples 76-81, wherein the docking system is configured to receive and hold the smartphone.

Example 95: The method of any of Examples 76-81, wherein the docking system is configured to receive and hold the cell phone.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subjectt matter.

BRIEF DESCRIPTION OF THE DRAWINGS

Example implementations disclosed herein are illustrated in the accompanying schematic drawings, which are for illustrative purposes only.

FIG. 3 illustrates the implementation of the handheld ophthalmic device illustrated in FIGS. 1A-1C integrated with a first implementation of a stand.

DETAILED DESCRIPTION OF EMBODIMENTS

Figures 1A, 1B, 1C:
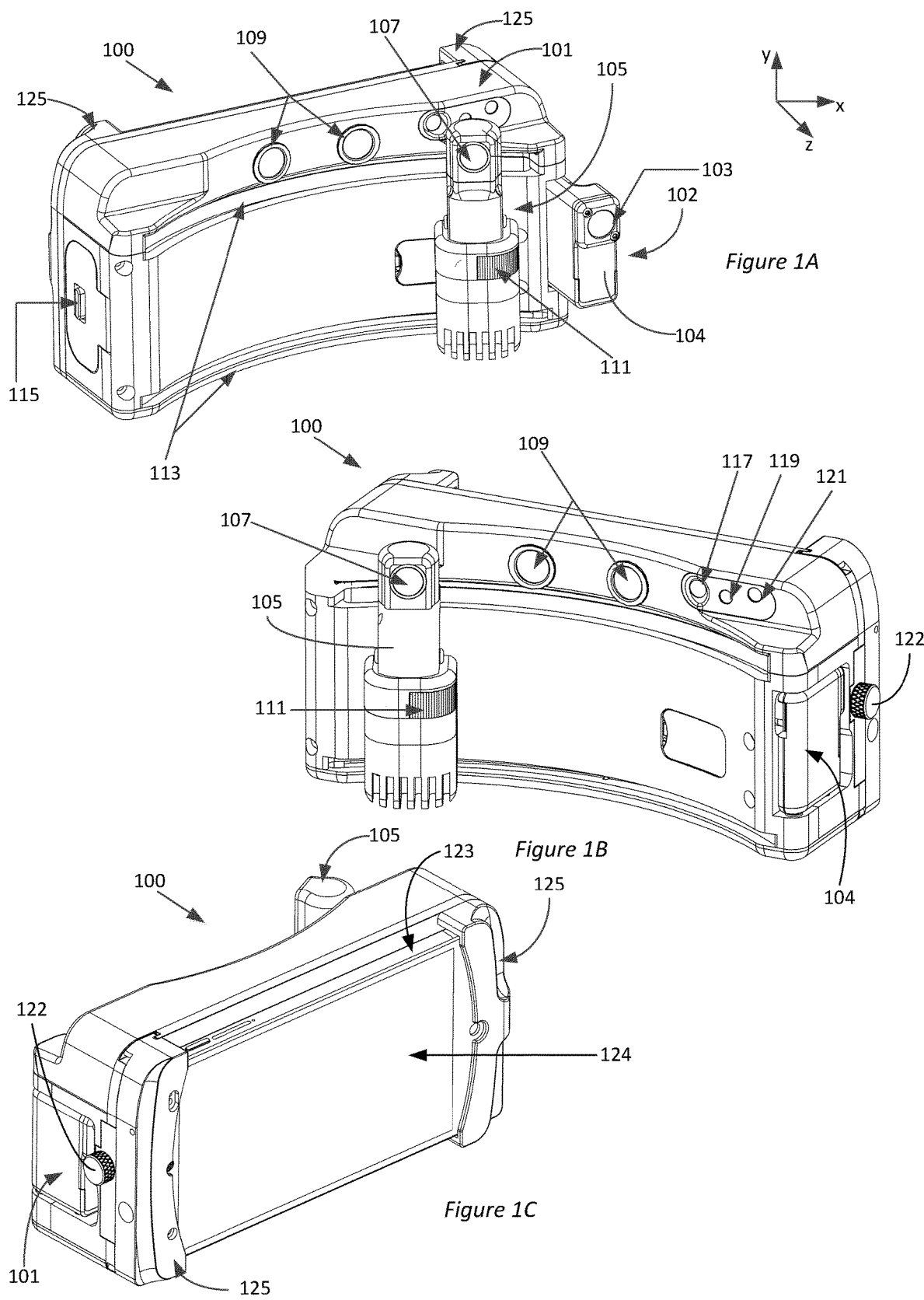
FIGS. 1A and 1B illustrate a front view of an implementation of the handheld ophthalmic device.
FIG. 1C illustrates a rear view of the implementation of the handheld ophthalmic device illustrated in FIGS. 1A and 1B.

This application contemplates a handheld ophthalmic device that is configured for use possibly in an outdoor or remote setting (e.g., a battlefield or a remote area) to obtain data and/or images (e.g., video images) of eyes and/or the face of one or more individuals at the outdoor or remote location. The data and/or images obtained by the handheld ophthalmic device can be used for on-site diagnosis and may also be transmitted to a health care professional, a doctor, a clinician, an ophthalmologist or an optometrist located a distance from the outdoor or remote setting for review, assessment, diagnosis, and/or possible treatment of the one or more individuals at the outdoor setting.

The handheld ophthalmic device is small and lightweight so as to be conveniently carried. Accordingly, a soldier, medic, or other personnel can conveniently store and transport the device on their person as they move about in the battlefield or remote setting. The handheld ophthalmic device can also be held in the hand to position the device in front of the eye of an injured person to obtain images or data to assist in evaluation of the condition of the person's eye.

Accordingly, the handheld ophthalmic device can be removably attached to a mobile communication device, such as, for example, a smartphone, a cell phone or an electronic tablet. Such mobile communication devices are typically carried by most people across the world, for example, soldiers, medics, rescue workers, firefighters, first responders, and include features useful for telemedicine applications. Cell phones, smart phones, and electronic tablets, for example, generally include displays, computing devices, and transmitters and receivers capable of transmitting and receiving voice, messages, images and data over long distances. The handheld ophthalmic device described herein can be configured to couple with such mobile communications devices and to use these features (e.g., displays, cellular network transmitters and receivers, etc.) instead of needing to include these features in the handheld ophthalmic device. The handheld ophthalmic device, by excluding a display and cellular transmitters and receivers can be made smaller and more compact. The operator or user, e.g., soldier, medic, rescue worker, firefighter, first responder, or other personnel, need therefore carry less total weight and bulk than if the handheld ophthalmic device included a display and cellular transmitter and receiver. Since it is expected that the operator or user will already be carrying a cell phone, the handheld ophthalmic device is configured to mate with that cell phone and use its display and cellular transmitter and receiver to perform telemedicine.

The mobile communication device, for example can transmit the data and/or images obtained by the handheld ophthalmic device. Additionally, it is contemplated that the display device (e.g., the touch-sensitive screen) incorporated in the smartphone, cell phone or electronic tablet can be used to display the data and/or images obtained by the handheld ophthalmic device as well as receive input and instructions from the operator or user. Furthermore, the data and/or images obtained by the handheld ophthalmic device can be stored in the memory of the smartphone, cell phone or electronic tablet. The smartphone, cell phone or electronic tablet can also be configured to provide guidance to an operator on how to obtain data and/or images of various portions of the eye using the ophthalmic device, provide information that may assist an operator in assessing the obtained data and/or images, and/or recommend treatment options. These and other concepts are discussed in detail below.

Overview of the Handheld Ophthalmic Device

FIGS. 1A and 1B illustrate a front view of an implementation of the handheld ophthalmic device 100. FIG. 1C illustrates a rear view of the implementation of the handheld ophthalmic device 100. The handheld ophthalmic device 100 comprises a mechanical assembly 101. In various implementations, the mechanical assembly 101 can have a size similar to that of the footprint of the mobile communications device and possibly at least less than 2 times, 1.5 times the size, 1.2 times, or about 1.0 times the footprint of the mobile communication device. Sizes in any range defined by any of these values are possible. The mechanical assembly 101, for example, can have a length along a direction parallel to the x-axis in a range between about 4 inches and about 8 inches, a height along a direction parallel to the y-axis between about 2 inches and about 5 inches, and a width along a direction parallel to the z-axis between about 1 inch and about 3 inches. For example, an implementation of the handheld ophthalmic device can have a length of about 6 inches, a height of about 3 inches and a width of about 2.1 inches. Other sizes and shapes however are possible. In addition, various designs will be light weight so as not to be burdensome for the soldier, medic, rescue worker, first responder, or firefighter, to carry around. In some implementations, for example, the handheld ophthalmic device 100 can weigh less than or equal to about 10 pounds, such as, for example less than or equal to about 5 pounds, less than or equal to about 3 pounds, or less than or equal to about 2 pounds or any weight in any range defined by these values. For example, an implementation of the handheld device 100 can weigh between about 1-1.5 lbs. For some designs, the footprint of the mechanical assembly 101 will be similarly shaped as the footprint of the mobile communication device, e.g., smart phone or cell phone. Accordingly, for some designes, the mechanical assembly 101 is configured, for example, as a substantially rectangular case with substantially rounded corners. The mechanical assembly 101 can comprise a light-weight rugged material that can withstand high temperatures, dry or humid conditions, and/or be moisture resistant. For some designs, the mechanical assembly 101 can comprise a polymer (e.g., silicone), plastic, metal, or a composite material.

The mechanical assembly 101 can comprise one or more (in some cases a plurality of) cameras and one or more (in some cases a plurality of) sources of illumination/light sources that are configured, for example, as an ophthalmoscope, a slit-lamp, a near-infrared pupillography device, and/or a facial/eye imaging device. Such diagnostic instruments are described in detail below. The light sources and cameras can be disposed to project light from the front side of the mechanical assembly 101 and/or capture light directed towards the front side of the mechanical assembly. In some implementations, the mechanical assembly 101 can further comprise a battery compartment 115 on a side of the mechanical assembly 101 that can provide electrical power to the various components (e.g., the cameras and the sources of illumination) integrated with the mechanical assembly 101. In some implementations, an optional secondary power source can be provided to provide electrical power to the various components (e.g., the cameras and the light sources). The secondary power source can comprise an auxiliary battery source, an electrical connection to connect to an electrical wall adapter or a photovoltaic cell.

The mechanical assembly 101 further comprises a docking system 125 on a back side of the mechanical assembly 101. The docking system 125 is configured to receive and hold a mobile communication device 123, such as, for example, a smartphone, a cell phone or an electronic tablet. The docking system 125 can comprise mating features such as mechanical brackets, recesses, slots or other features that are shaped and sized to receive and hold a mobile communication device 123, such as, for example, a smartphone, cell phone or electronic tablet. Other arrangements for coupling the mechanical assembly 101 to the mobile communication device 123 are possible. The docking system 125 can further comprise one or more securing features, such as, for example, mechanical fasteners, springs, screws, clamps or clasps to securely hold the mobile communication device 123, such as, for example, smartphone, cell phone or electronic tablet. The docking system 125 can be removably attached to the handheld ophthalmic device 100. Thus, in some implementations, a docking system 125 having a size that is matched to the size of the operator's smartphone, cell phone or electronic tablet can be selected for use. In various implementations, the docking system 125 can be repeatedly removed and attached to the rear side of different mobile communication devices opposite to a display screen 124 of the mobile communication device 123, such as, for example, different smartphones, cell phones or electronic tablets.

Accordingly, when mechanically attached to the docking system 125, the display screen 124 of the mobile communication device 123, such as, for example, smartphone, cell phone or electronic tablet is opposite the front side of the mechanical assembly 101 through which or towards which the light sources and the cameras are configured to project and/or capture light. Likewise, the display screen 124 of the mobile communications device 123 is outwardly facing and exposed so as be visible to the operator/user and provide access to touch (for example, in the case of a touch screen display).

The mechanical assembly 101 can comprise electronics in electrical communication with a memory device. The electronics can comprise at least one of a transmitter, a receiver, an electrical interconnect, an electrical conductor or combinations thereof that is configured to transmit and receive information to and/or from the mobile communication device 123 over distances less than or equal to about 100-120 feet. For example, the electronics can comprise wireless or BLUETOOTH communication system that is capable of transmitting and receiving information to and from the mobile communication device 123 wirelessly. Such wireless communication between the handheld ophthalmic device and the mobile communication device can be provided despite the handheld ophthalmic device and the mobile communication device being physically coupled together and thus in physical contact. As another example, the electronics can be configured to provide a wired connection between the mechanical assembly 101 and the mobile communication device 123. As yet another example, the mechanical assembly 101 can comprise a USB or a mini/micro USB connector that can be connected to the mobile communication device 123, for example, with a USB or a mini/micro USB cable. Other types of USB connections or other connections for data transfer can also be used. In some implementations, the electronics and the memory device can be integrated on a circuit board that is assembled with the mechanical assembly 101.

Ophthalmoscope

As discussed above, the mechanical assembly 101 comprises cameras and illumination sources that are configured to function as various optical diagnostic instruments. One of the optical diagnostic instruments contemplated in this application is an ophthalmoscope 102. In various implementations, at least a first camera is coaxially disposed or substantially coaxially disposed with at least a first illumination source and configured as the ophthalmoscope 102. The first camera and the first source of illumination are disposed in a compartment 104 on one side of the mechanical assembly 101. For example, the compartment 104 can be disposed on a side of the mechanical assembly 101 opposite the side on which the battery compartment 115 is disposed. The compartment 104 of mechanical assembly 101 can be configured as a hinged compartment that can be disposed in a first open position when the ophthalmoscope 102 is in use and in a second closed position when the ophthalmoscope 102 is not in use. In the second closed position, the first camera and the first source of illumination can be disposed within a recess of the mechanical assembly 101. The mechanical assembly 101 can comprise a lock 122 to lock the compartment 104 when the ophthalmoscope 102 is not used. The compartment 104 comprises a window or an aperture or an opening 103 through which light from the first source of illumination is emitted towards the eye of a subject facing the front side of the mechanical assembly 101 when the compartment 104 is positioned in the first open position. The window, the aperture, or the opening 103 can be situated such that it is imperceptible and protected when the compartment 104 is positioned in the second closed position. In other implementations, a door may open and close to permit the first camera to capture images and to protect the first camera when not used. Other variations in design are also possible.

The first source of illumination can comprise one or more of the following one or more light emitting diodes (LEDs), halogen/argon light, incandescent light, organic light emitting diode (OLED) source or its variants. The first source of illumination can be powered by the batteries disposed in the battery compartment 115 or the optional secondary power source. In some designs, the first source of illumination can be configured to direct white light through the aperture 103 towards the eye of the subject facing the front side of the mechanical assembly 101 when the compartment 104 is disposed in the first open position and the ophthalmoscope 102 is configured to be used. In some implementations, the mechanical assembly 101 can comprise a button or a switch that can be used to turn on/turn off or control the intensity of light emitted from the first source of illumination. In some implementations, the operation of the first source of illumination can be controlled via a software application (e.g., an "app") executed by an electronic processing system. The software application can be executed by the electronic processing system of the mobile communication device 123 (e.g., cell phone), the electronics of the handheld ophthalmic device 100 or a combination of the electronic processing system of the mobile communication device 123 (e.g., cell phone) and the electronics of the handheld ophthalmic device 100. As another example, electronic processing system of the mobile communication device 123 can execute a software application (e.g., "app") that displays a control panel on the display screen 124 of the mobile communication device 123. An operator can turn on or turn off the first light illumination source and/or control the intensity of light emitted from the first light illumination source via the control panel displayed on the display screen 124 on the cell phone, smart phone, or electronic tablet.

For some designs, the first camera can be a variable or fixed focus camera. The first camera may have a working distance between about 3 inches and about 6 inches in some designs. As discussed above, the first camera can be powered by the batteries disposed in the battery compartment 115 or the optional secondary power source. The first camera is configured to capture images of the fundus, the retina, the optic nerve, the vitreous humor and/or other internal structures of the subject's eye that are illuminated by the light from the first source of illumination, for example, when the compartment 104 is disposed in the first open position and the ophthalmoscope 102 is configured to be used. In some implementations, the mechanical assembly 101 can comprise a button or a switch that can be used to turn on/turn off the first camera, adjust the focus of the first camera and/or capture one or more images of the fundus and/or internal structures of the subject's eye. In some implementations, the operation of the first camera can be controlled via a software application (e.g., an "app") executed by an electronic processing system. The software application can be executed by the electronic processing system of the mobile communication device 123 (e.g., cell phone), the electronics of the handheld ophthalmic device 100 or a combination of the electronic processing system of the mobile communication device 123 (e.g., cell phone) and the electronics of the handheld ophthalmic device 100. For example, electronic processing system of the mobile communication device 123 can execute a software application (e.g., "app") that displays a control panel on the display screen 124 of the mobile communication device 123. An operator can turn on or turn off the first camera, adjust the focus of the first camera and/or capture one or more images of the fundus and/or internal structures of the subject's eye via the control panel displayed on the display screen 124. The application can also display images such as live or real time images obtained from the first camera to the viewer via the display screen 124. In some implementations, the operator can adjust various parameters of the first camera (e.g., focus, zoom, contrast ratio, or combinations thereof) based on a live or real time image of the fundus and/or internal structures of the subject's eye displayed on the display screen 124. It is noted that the first camera is different from a camera or an imaging device in the mobile communication device 123. For example, cell phones, smart phones, electronic tablets frequently have integrated cameras. However, this application contemplates that in certain implementations no camera or imaging device integrated or incorporated in the mobile communication device 123 is used as the first camera configured to capture one or more images of the fundus and/or internal structures of the subject's eye. As discussed above, one or more images of the fundus and/or internal structures of the subject's eye captured by the first camera are transported to the mobile communication device 123 by the electronics in the handheld ophthalmic device for display, storage and/or transmission to an ophthalmologist, optometrist, or other party located remotely.

Slit Lamp

Figure 2A:
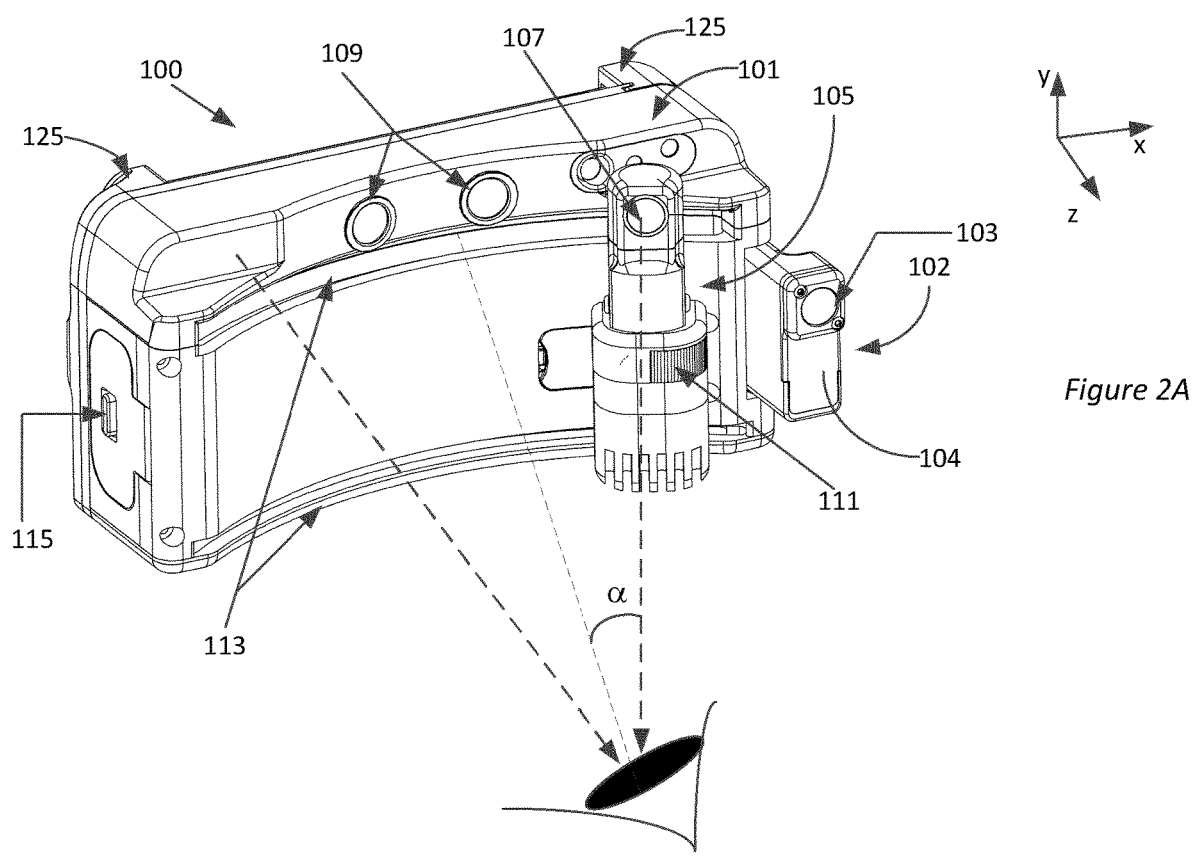
FIG. 2A illustrates the path of light emitted from the slit lamp portion of the handheld ophthalmic device illustrated in FIGS. 1A-1C.

Another of the optical diagnostic instruments contemplated in this application is a slit lamp comprising at least a second illumination source. The slit-lamp is configured to examine the cornea, iris, lens, conjunctiva and/or eyelids of the subject facing the front side of the mechanical assembly 101. In some implementations, the slit lamp may additionally include a second camera. The second source of illumination is disposed in a canister, compartment, or housing 105. The canister, compartment, or housing 105 comprises a window 107 through which light from the second source of illumination is emitted. A mirror can be provided in the canister, compartment, or housing 105 to fold the optical path along the length of the canister, compartment, or housing 105. The mirror can be inclined at an angle (e.g., 45 degrees) with respect to a vertical axis of the canister, compartment, or housing 105. In some implementations, multiple optical elements may be included along the length of the canister, compartment, or housing 105. The canister, compartment, or housing 105 includes therein an aperture and a lens or lens system configured to form a focused image of the aperture on the eye. In some designs, the canister, compartment, or housing 105 may comprise an aperture selector 111. The aperture selector 111 can comprise a plurality of apertures with different shapes and/or sizes, such as, for example, rectangular or circular apertures. The operator can select a desired aperture shape (e.g., rectangular or circular) and/or size to perform the slit lamp examination. The lens or lens system is configured to focus an image of the aperture at a working distance between about 3 inches and 6 inches from the window 107. The lens or lens system can have a depth of focus between about 5 mm and about 12 mm. For example, the depth of focus can be within ±5 mm of the working distance. The subject's eye is positioned at the working distance so that the image of the aperture projected onto the subject's eye through the window 107 is in focus. Accordingly, in various implementations, the subject's eye can be considered to be in the conjugate plane of the aperture. The height of the image of a rectangular aperture (which may comprise a cross-section of the beam) in a plane at the working distance can be configured to extend across the entire height of the subject's eye or cornea. The width of the image of the rectangular aperture (which may comprise a cross-section of the beam) in a plane at the working distance can be configured to be between about 0.5 mm and about 2.0 mm. The diameter of the image of a circular aperture (which may comprise a cross-section of the beam) in a plane at the working distance can be between about 5 mm and about 12 mm. Accordingly, when the slit lamp is in use, light from the second source of illumination that passes through the selected aperture is focused on various portions of the eyelids, lens, conjunctiva, cornea and/or iris of the subject as shown in FIG. 2A.

The second source of illumination may be configured to output light in different wavelength ranges. For example, the second source of illumination can be configured to output white light. As another example, the second source of illumination can be configured to output a colored light (e.g., green, yellow or blue). In various implementations, one or more fluorophores or fluorescent agents can be applied to the subject's eye prior to the slit lamp examination. In such implementations, the second source of illumination may be configured to emit wavelengths of light that excite fluorescence from the one or more applied fluorophores or fluorescent agents.

It can be advantageous to focus light from the second source of illumination on the various portions of the cornea, iris, lens, conjunctiva, and/or eyelids of the subject from a plurality of directions. In various implementations, for example, light from the second source of illumination is configured to be swept by moving the canister, compartment or housing 105 along the tracks or rails such that light is incident on the subject's eye over a range of oblique angles (a) between at least about ±90 degrees with respect to an optical axis of the subject's eye which is an imaginary line that passes through the center of the cornea and the natural lens of the eye. For example, light from the second source of illumination can be configured to be incident on the subject's eye over a range of oblique angles (a) between at least about ±60 degrees, at least ±45 degrees, or at least ±30 degrees, or at least ±25 degrees, or at least ±15 degrees with respect to the optical axis. Other ranges defined by any of these values are also possible. Accordingly, the canister, compartment or housing 105 can be configured to be mechanically laterally translated across the length of the mechanical assembly 101 or portion thereof. To advantageously allow the light from the second source of light to be in focus on the eye as the canister, compartment or housing 105 is translated across the length of the mechanical assembly 101, the canister, compartment or housing 105 may be disposed on a curved track or rail and the eye of the subject is positioned at approximately the center of curvature of track or rail. Similarly the front side of the mechanical assembly 101 may be curved. Accordingly, the light from the second source of illumination may be directed along a radial direction towards a common location where the subject's eye is located as shown in FIG. 2A. The light from the window 107 may be focused on this location and may remain in focus as the canister, compartment or housing 105 comprising the one or more apertures is translated along the track or rail. In various implementations, the radius of curvature of the track or rail and/or front curved side of the mechanical assembly 101 can be between about 3 inches and 5 inches such that the subject's eye is positioned at a distance between about 3 and 5 inches from the front side of the mechanical assembly 101 when the slit lamp examination of the subject's eye is being performed. Similarly, the light from the slit lamp may be focused between 3 and 5 inches from the slit lamp (e.g., the cannister).

As discussed above, the second source of illumination can be powered by the batteries disposed in the battery compartment 115 or the optional secondary power source. In some implementations, the mechanical assembly 101 can comprise a button or a switch that can be used to turn on/turn off or control the intensity of light emitted from the second source of illumination. In some implementations, the operation of the second source of illumination can be controlled via a software application (e.g., an "app") executed by an electronic processing system. The software application can be executed by the electronic processing system of the mobile communication device 123 (e.g., cell phone), the electronics of the handheld ophthalmic device 100 or a combination of the electronic processing system of the mobile communication device 123 (e.g., cell phone) and the electronics of the handheld ophthalmic device 100. For example, electronic processing system of the mobile communication device 123 can execute a software application (e.g., "app") that displays a control panel on the display screen 124 of the mobile communication device 123. An operator can turn on or turn off the second source of illumination, control the intensity of light emitted from the second source of illumination and/or change the wavelength of the light emitted from the second source of illumination via the control panel displayed on the display screen 124.

In some cases, the operator may observe the subject eye when the subject's eye is illuminated with light from the slit lamp. The canister, compartment or housing 105 comprising the one or more apertures may be translated by the user/operator along the track or rail to sweep the light incident on the eye through a range of angles such that the light is incident on different portions of the eye. The operator may be able to see different sections of the eye using the slit lamp. The operator may visually observe the subject's eye illuminated with the slit lamp directly using the operator's unaided eye in some cases.

In other cases, the at least second camera associated with the slit lamp is configured to capture images of various portions of the subject's eye that are illuminated by light from the second source of illumination. In various implementations of the handheld ophthalmic device 100, the second camera associated with the slit lamp can be a unitary camera or be a part of a multi-camera imaging system. For example, in the implementation of the handheld ophthalmic device 100, illustrated in FIGS. 1A-1C, the second camera can be a part of a stereoscopic imaging system 109. The second camera and/or the other cameras of the multi-camera imaging system can be fixed focus or variable focus cameras. The focus or working distance of the second camera and/or the other cameras of the multi-camera imaging system can be between about 3 inches and about 6 inches. In the implementation of the handheld ophthalmic device 100, illustrated in FIGS. 1A-1C, the stereoscopic imaging system 109 can comprise a pair of fixed focus cameras. The stereoscopic imaging system 109 provides the handheld ophthalmic device 100 with the ability to capture three-dimensional image of the illuminated portions of the subject's cornea, iris, lens, conjunctiva, and/or eyelids. In some implementations, the second camera is focused on the same location as the location at which the image of the aperture is focused. For example, the second camera may be focused at the working distance from the window 107 where the image of the aperture is focused. Additionally, as the canister, compartment or housing 105 comprising the one or more apertures are translated along the track or rail, the second camera remains in focus on the same location as the slit lamp.

As discussed above, the second camera and/or the other cameras of the multi-camera imaging system can be powered by the batteries disposed in the battery compartment 115 or the optional secondary power source. In some implementations, the mechanical assembly 101 can comprise a button or a switch that can be used to turn on/turn off the second camera and/or the other cameras of the multi-camera imaging system, adjust the focus of the second camera and/or the other cameras of the multi-camera imaging system and/or capture one or more images of the various portions of the cornea, iris, lens, conjunctiva, and/or eyelids of the subject that are illuminated by light from the second source of illumination. In some implementations, the operation of the second camera and/or the other cameras of the multi-camera imaging system can be controlled via a software application (e.g., an "app") executed by an electronic processing system. The software application can be executed by the electronic processing system of the mobile communication device 123 (e.g., cell phone), the electronics of the handheld ophthalmic device 100 or a combination of the electronic processing system of the mobile communication device 123 (e.g., cell phone) and the electronics of the handheld ophthalmic device 100. For example, electronic processing system of the mobile communication device 123 can execute a software application (e.g., "app") that displays a control panel on the display screen 124 of the mobile communication device 123. An operator can turn on or turn off the second camera and/or the other cameras of the multi-camera imaging system, adjust the focus of the second camera and/or the other cameras of the multi-camera imaging system and/or capture one or more images of the various portions of the cornea, iris, lens, conjunctiva, and/or eyelids of the subject that are illuminated by light from the second source of illumination (e.g., slit lamp) via the control panel displayed on the display screen 124. The application can also display images such as live or real time images obtained from the second camera to the viewer via the display screen 124. In some implementations, the operator can adjust the position of the handheld ophthalmic device 100 from the subject's eye, adjust various parameters of the second camera and/or the other cameras of the multi-camera imaging system (e.g., focus, zoom, contrast ratio, or combinations thereof) based on a live or real time image of the individual's eye displayed on the display screen 124.

It is noted that the second camera and/or the other cameras of the multi-camera imaging system is different from a camera or an imaging device integrated with and/or incorporated in the mobile communication device 123. This application contemplates that in certain implementations no camera or imaging device of the mobile communication device 123 is used as the second camera and/or the other cameras of the multi-camera imaging system to capture one or more images of the portions of individual's eye that are illuminated by the second source of illumination.

As discussed above, one or more images of the portions of subject's eye that are illuminated by the second source of illumination and captured by the second camera and/or the other cameras of the multi-camera imaging system can be transported to the mobile communication device 123 by the electronics for display, storage and/or transmission, e.g., to a health care professional, a doctor, an ophthalmologist, optometrist or other party, located remotely.

Near Infrared Pupillography and/or Facial Imaging

Yet another optical diagnostic instrument contemplated in this application is near infrared (NIR) pupillography and/or facial imaging. FIGS. 2B-1 to 2B-4 illustrate different implementations of integrating the different components that are used for NIR pupillography and/or facial imaging. A third of the plurality of possible cameras 209 and a third of the plurality of possible illumination sources 213 can be configured to perform NIR pupillography. The third source of illumination 213 can comprise a light emitting diode (LED) configured to emit radiation in near infrared wavelengths, such as, for example, between about 700 nm and about 1100 nm. For example, the third source of illumination 213 can be an LED configured to emit light at 850 nm. As another example, the third source of illumination 213 can be an LED configured to emit light at 740 nm. Other wavelengths or ranges of wavelengths, for example, in the near infrared (NIR) range, can be used in different implementations. The third camera 209 can be a camera that is configured to receive and detect near infrared light as well as white light. In an implementation of the ophthalmic device 100, the third camera 209 can be a video camera that is sensitive to near infrared light in a wavelength range between 700 nm and about 1100 nm. For example, the third camera 209 can be a video camera that is sensitive to near infrared light at 740 nm and/or at 850 nm.

In some implementations, the third camera 209 is a fixed focus camera or configured as variable focus camera that can be configured to focus at the location where the eye of the subject is to be positioned. In some, cases, that location is the same location as for other of the cameras, such as the first and/or second camera. Accordingly, in various implementations, more than one of the cameras are focused on the same location where the eye will be situated. This may include, for example, the slit lamp camera, e.g., the second camera, which may be at the same focus for a variety of locations of the slit lamp camera and slit lamp on the track or rail.

In certain designs, the mechanical assembly 101 can comprise a fourth of the plurality of possible illumination sources 211 configured to provide white light for imaging of the face and/or eye. The fourth source of illumination 211 can comprise one or more LEDs configured to provide white light or a flash lamp. In the design illustrated, the third camera 209 and the third and the fourth sources of illumination 213 and 211 are integrated in an upper corner of the mechanical assembly 101 as shown in FIGS. 2B-1, 2B-2 and 2B-3. Integrating the third camera 209 and the third and the fourth sources of illumination 213 and 211 in the upper corner of the mechanical assembly 101 can in some circumstances make the most efficient use of the available space of the mechanical assembly 101.

Figures 1, 2B:
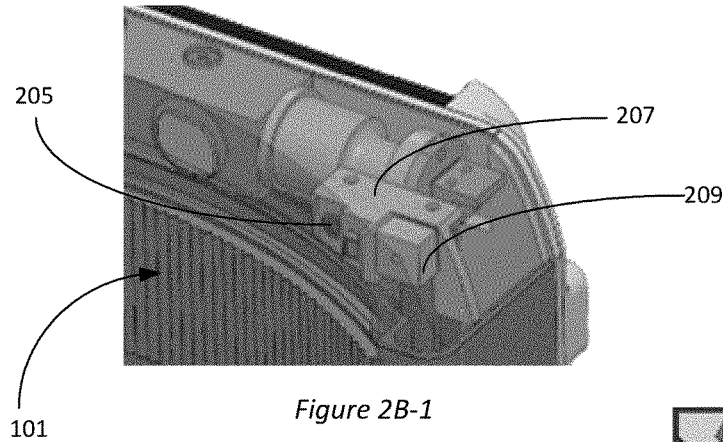
FIGS. 2B-1 to 2B-4 illustrate different implementations of integrating the various components that can be used for NIR pupillography and/or facial imaging.
Figures 2, 2B:
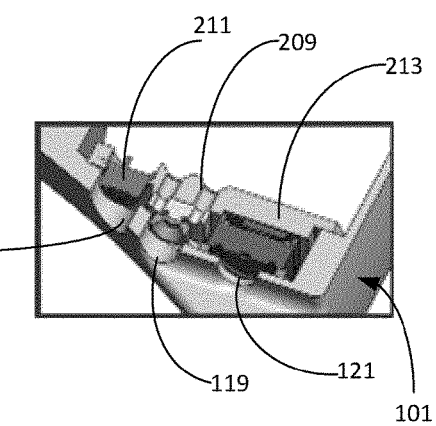

In some implementations, the third camera 209 and an illumination unit 205 comprising the third and the fourth sources of illumination 213 and 211 are integrated on a mount 207 that is disposed in the upper corner of the mechanical assembly 101 as shown in FIG. 2B-1. In some implementations, the third camera 209, the third source of illumination 213 and the fourth source of illumination 211 can be disposed within a volume in an upper corner of the mechanical assembly 101 as shown in FIG. 2B-2. Apertures, exit windows or openings 117, 119 and 121 are provided in the front side of the mechanical assembly 101 corresponding to the light emitting aperture, exit window or opening of the third source of illumination 213 and the fourth source of illumination 211 and the light receiving aperture of the third camera 209, respectively.

Figures 2, 2B, 3:
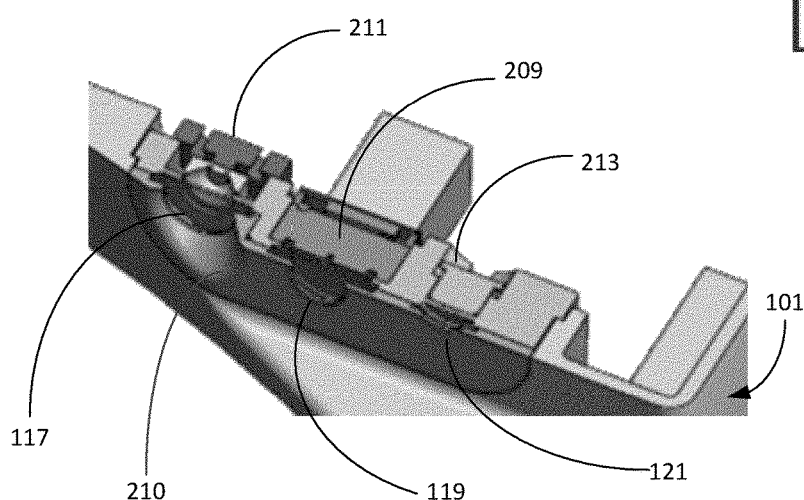
Figures 2, 2B, 3, 4:
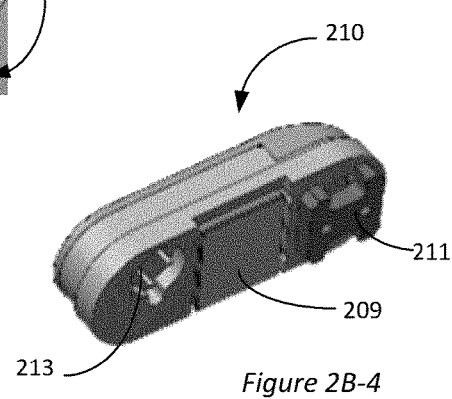
Figure 3:
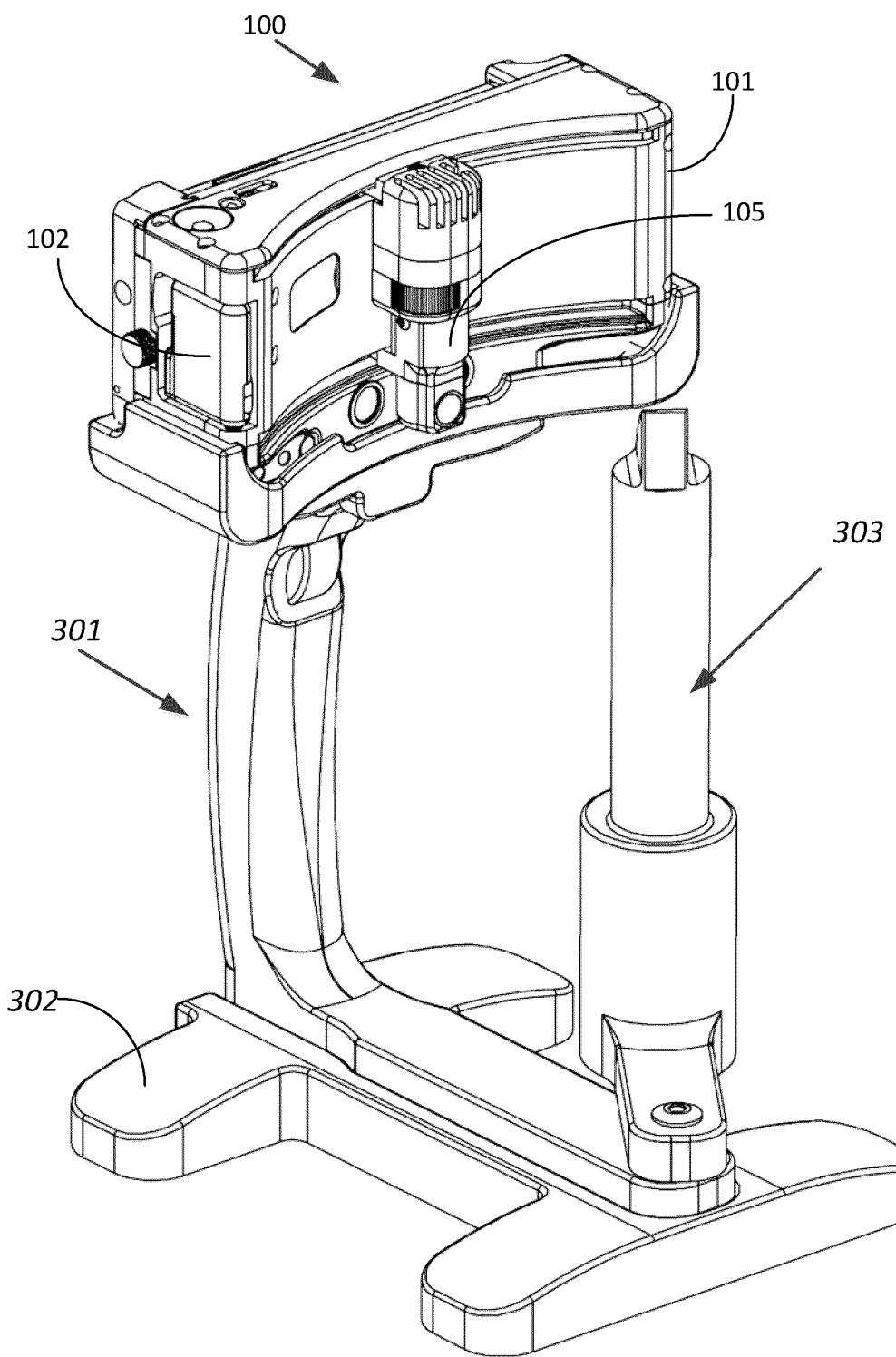

In some other implementations, the third camera 209, the third source of illumination 213 and the fourth source of illumination 211 can be integrated in a chassis 210 that is configured to be disposed in an upper corner of the mechanical assembly 101 as shown in FIG. 2B-3. FIG. 2B-4 illustrates a rear view of the chassis 210. A front surface of the chassis can comprise apertures, exit windows or openings 117, 119 and 121 corresponding to the light emitting aperture, window or opening of the third source of illumination 213 and the fourth source of illumination 211 and the light receiving window of the third camera 209 respectively.

As discussed above, the third and/or fourth sources of illumination 213 and 211 can be powered by the batteries disposed in the battery compartment 115 or the optional secondary power source. In some implementations, the mechanical assembly 101 can comprise a button or a switch that can be used to turn on/turn off or control the intensity of light emitted from the third and/or fourth sources of illumination 213 and 211. In some implementations, the operation of the third and/or fourth sources of illumination 213 and 211 can be controlled via a software application (e.g., an "app") executed by an electronic processing system. The software application can be executed by the electronic processing system of the mobile communication device 123 (e.g., cell phone), the electronics of the handheld ophthalmic device 100 or a combination of the electronic processing system of the mobile communication device 123 (e.g., cell phone) and the electronics of the handheld ophthalmic device 100. For example, electronic processing system of the mobile communication device 123 can execute a software application (e.g., "app") that displays a control panel on the display screen 124 of the mobile communication device 123. An operator can turn on or turn off the third and/or fourth sources of illumination 213 and 211, control the intensity of light emitted from the third and/or fourth sources of illumination 213 and 211 and/or change the wavelength of the light emitted from the third and/or fourth sources of illumination 213 and 211 via the control panel displayed on the display screen 124.

NIR pupillography is performed in a darkened room with reduced ambient light to prevent the pupil of the subject's eye from constricting. Near infrared light from the third source of illumination 213 is directed towards the individual's eye and the individual's pupillary reaction is captured by the third camera 209. To image the face and/or eyes of the individual, visible light from the fourth source of illumination 211 may be directed towards the individual and one or more images of the subject's face and/or eyes can be captured by the third camera 209.

As discussed above, the third camera 209 can be powered by the batteries disposed in the battery compartment 115 or the optional secondary power source. In some implementations, the mechanical assembly 101 can comprise a button or a switch that can be used to turn on/turn off the third camera 209, adjust the focus of the third camera 209 and/or capture a video of the individual's pupillary reaction to the near infrared light and/or capture still images of the individual's face and/or eyes. In some implementations, the operation of the third camera 209 can be controlled via a software application (e.g., an "app") executed by an electronic processing system. The software application can be executed by the electronic processing system of the mobile communication device 123 (e.g., cell phone), the electronics of the handheld ophthalmic device 100 or a combination of the electronic processing system of the mobile communication device 123 (e.g., cell phone) and the electronics of the handheld ophthalmic device 100. For example, electronic processing system of the mobile communication device 123 can execute a software application (e.g., "app") that displays a control panel on the display screen 124 of the mobile communication device 123. An operator can turn on or turn off the third camera 209, adjust the focus of the third camera 209 and/or capture one or more videos/images of the subject's face and/or eyes via the control panel displayed on the display screen 124. The application can also display images such as live or real time images obtained from the third camera to the viewer via the display screen 124. In some implementations, the operator can adjust the position of the handheld ophthalmic device 100 from the subject's eye, adjust various parameters of the third camera 209 (e.g., focus, zoom, contrast ratio, or combinations thereof) from a live or real time image of the individual's eye displayed on the display screen 124. It is noted that the third camera 209 is different from a camera or an imaging device integrated with or incorporated in the mobile communication device 123. This application contemplates that in various implementations no camera or imaging device in the mobile communication device 123 is used for near infrared pupillography and/or imaging of the eye/face.

The native camera integrated with or incorporated in the mobile communication device 123 can be sensitive to back reflections from the flash reflecting off surrounding surfaces. Accordingly, the quality of images obtained by the plurality of cameras integrated with the mechanical assembly 101 can be higher than the quality of the images obtained by the native camera integrated with or incorporated in the mobile communication device 123 when attached to the rear side of the mechanical assembly 101 as discussed herein due to back reflections from the flash reflecting off the surfaces of the mechanical assembly 101. Furthermore, use of the native camera in the mobile communication device 123 to capture images of the individual's eyes/face may disadvantageously lead to an increase in the size of the mechanical assembly 101 to accommodate the large aperture that may be used to accommodate the large clear aperture of the native camera in the mobile communication device 123. As discussed above, the one or more videos/images captured by the third camera 209 are transported to the mobile communication device 123 by the electronics for display, storage and/or transmission to a health care professional, a doctor, an ophthalmologist, optometrist or other party located remotely.

Ophthalmic Device with a Stand

Figure 4A:
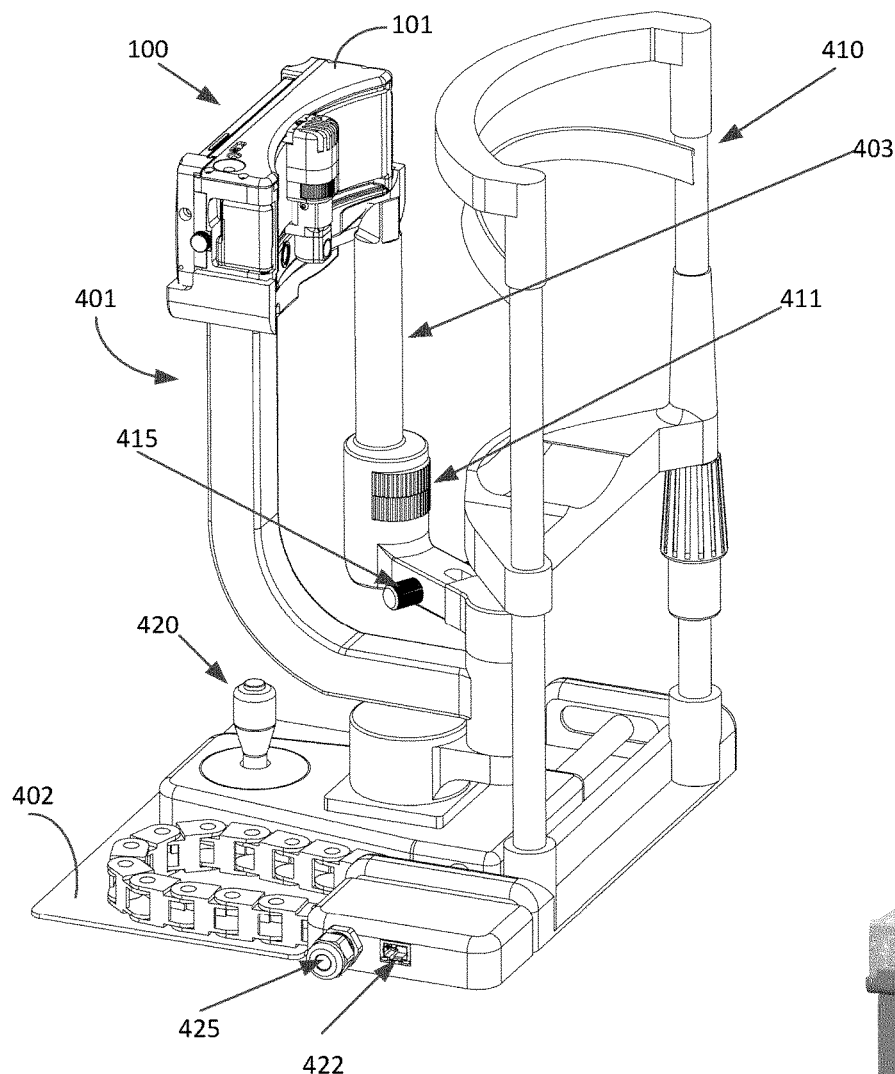
FIGS. 4A and 4B illustrate the implementation of the handheld ophthalmic device illustrated in FIGS. 1A-1C integrated with a second implementation of a stand.

The handheld ophthalmic device 100 can be used with a stand. The stand can be a light weight portable stand 301 as shown in FIG. 3 or a table top stand 401 that is heavier and not configured to be as easily moved as shown in FIG. 4A. The stand (e.g., stand 301 or stand 401) can comprise a base (e.g., base 302 or base 402) that can be placed on a table top or a desktop. The stand (e.g., stand 301 or stand 401) can further comprise a platform above the base (e.g., base 302 or base 402). The handheld ophthalmic device 100 can be mechanically attached to the platform and removably detached via fastening/locking devices, such as, for example, fasteners such as, screws, clips, latches, or combinations thereof. The handheld ophthalmic device 100 integrated with the stand (e.g., stand 301 or stand 401) can be configured for use in a field hospital or a make-shift hospital setting. The stand (e.g., stand 301 or stand 401) can provide a stable platform for mounting the handheld ophthalmic device 100 so that the operator does not need to hold the handheld ophthalmic device 100 in his or her hand when imaging the subject's eye or collecting data on the subject. In comparison to the handheld ophthalmic device 100, however, the stand (e.g., stand 301 or stand 401), may be less convenient for the soldier, medic, first responder, firefighter, or other personnel to carry around in the battle field, accident or disaster site or other remote location. The stand (e.g., stand 301 or stand 401) may be stored and used in a facility such as a field hospital, local clinic, etc.

The stand (e.g., stand 301 or stand 401) can further comprise a secondary slit lamp (e.g., slit lamp 303 or slit lamp 403). The secondary slit lamp (e.g., slit lamp 303 or slit lamp 403) can potentially provide a wider angular range of operation (e.g., wider range of swing angles a) as compared to the slit lamp of the handheld ophthalmic device 100. In addition or in the alternative, the secondary slit lamp (e.g., slit lamp 303 or slit lamp 403) can be configured to provide additional aperture sizes, brighter illumination and/or additional wavelengths thereby expanding over the functionality provided by the slit lamp of the handheld ophthalmic device 100. It is noted that when the handheld ophthalmic device 100 is attached to the stand (e.g., stand 301 or stand 401), the secondary slit lamp (e.g., slit lamp 303 or slit lamp 403) may be used to perform the slit lamp examination. It is contemplated in certain implementations, that the slit lamp of the handheld ophthalmic device 100 is not used when the handheld ophthalmic device 100 is attached to the stand (e.g., stand 301 or stand 401).

In some implementations, the secondary slit lamp (e.g., slit lamp 303 or slit lamp 403) can further comprise an aperture selector (e.g., aperture selector 411) configured to alter the size or shape of the image of the aperture that is focused at the working distance from the window provided with the secondary slit lamp (e.g., slit lamp 303 or slit lamp 403). The width, diameter or aspect ratio of the aperture of the secondary slit lamp (e.g., slit lamp 303 or slit lamp 403) may, for example, be altered with the aperture selector (e.g., aperture selector 411).

The secondary slit lamp (e.g., slit lamp 303 or slit lamp 403) and the slit lamp of the handheld ophthalmic device 100 can occupy the same or substantially overlapping swing path and may have coincident centers of rotation. Accordingly, the secondary slit lamp (e.g., slit lamp 303 or slit lamp 403) can further comprise a knob (e.g., knob 415 as shown in FIG. 4A) that can be used to manipulate the position of the secondary slit lamp (e.g., slit lamp 303 or slit lamp 403) as it is moved past the slit lamp of the handheld ophthalmic device 100 so as to avoid striking the slit lamp of the handheld ophthalmic device 100. For example, the knob (e.g., knob 415) can be used to move the secondary slit lamp (e.g., slit lamp 303 or slit lamp 403) towards the subject (or the chin rest 410 described below) and away from the handheld ophthalmic device 100 as the secondary slit lamp (e.g., slit lamp 303 or slit lamp 403) is moved past the slit lamp of the handheld ophthalmic device 100.

One or more of the plurality of cameras of the handheld ophthalmic device 100 (e.g., the stereoscopic imaging system 109) can be used to capture images of the individual's eye when the secondary slit lamp (e.g., slit lamp 303 or slit lamp 403) is used to perform a slit lamp examination of the individual's eye. In some implementations, the stand (e.g., stand 301 or stand 401) can further comprise controls that can be used to control/trigger the handheld ophthalmic device 100 and/or the secondary slit lamp (e.g., slit lamp 303 or slit lamp 403). For example, the stand (e.g., stand 301 or stand 401) can further comprise controls and/or electronics that can initiate the slit lamp examination of the eye, the capture of images and/or the transfer the captured images. Accordingly, the stand may in some designs include input controls, electronics (e.g., motors, control, and/or interfacing electronics, etc.) to control any one or more of the movement/translation of the secondary slit lamp (e.g., slit lamp 303 or slit lamp 403), the activation of the slit lamp, the activation or control of other cameras and/or light sources, or the interaction with the mobile communication device. In some implementations, however, the secondary slit lamp 303 is moved manually (e.g., by hand by the operator) and need not include an actuator (e.g., motor) and electronic movement controls (e.g., joystick).

Figure 4B:
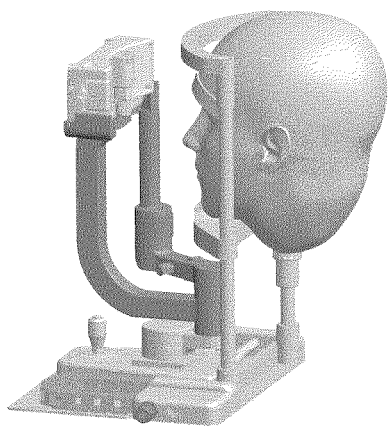

In some implementations, the stand (e.g., the stand 401) can comprise a chin rest 410 as shown in FIGS. 4A and 4B. A subject whose eyes are to be examined can place his/her chin on the chin rest 410 and an operator can perform various diagnostic tests on the subject's eyes.

In some implementations, the stand (e.g., the stand 401) can comprise a movement assembly 420 as shown in FIG. 4A. The movement assembly 420 can be a joystick that can be used to laterally translate the secondary slit lamp (e.g., secondary slit lamp 403).

In some implementations, the stand (e.g., the stand 401) can further comprise an electrical connection (e.g., electrical connection 425) that can be used to power the components of the handheld ophthalmic device 100 and/or the secondary slit lamp (e.g., slit lamp 303 or slit lamp 403). The electrical connection (e.g., electrical connection 425) can be configured to connect to an electrical wall socket. The stand (e.g., stand 401) can further comprise an Ethernet port that can be used to transmit the video/still images captured by one or more of the plurality of cameras of the handheld ophthalmic device 100 to a healthcare professional, a doctor, an ophthalmologist, an optometrist, or another party located remotely for further review and/or to a storage device. In such implementations, the mobile communication device 123 need not be used to transmit the captured video/still images. In various implementations, the stand (e.g., the stand 401) can further comprise controls that can be used to trigger the handheld ophthalmic device 100. For example, the stand (e.g., the stand 401) can comprise buttons/toggles/switches that can initiate the various diagnostic tests of the eye, capture one or more images of the eye, and/or transfer the captured images. In some implementations, the stand (e.g., the stand 401) can comprise a video port, such as, a USB or a HDMI connector configured to be connected to an external display device, such as, for example, a TV screen, a wall display, a large screen display, etc. In such implementations, the captured video/still images can be viewed on the external display device instead of the display screen of the mobile communication device 123. As discussed above, the stand in various implementations, such as in FIG. 3, can be configured to be simpler, lighter and/or more portable by excluding components such as one or more of motors, movement assemblies, communication electronics, chin rest, etc.

Operation Modes of the Mobile Communication Device

As discussed herein, the mobile communication device 123 can be configured to receive one or more videos/images captured by one or more of the plurality of cameras of the handheld ophthalmic device 100. The received one or more videos/images can be stored in a memory device in the mobile communication device 123, displayed to the operator and/or transmitted to an ophthalmologist, optometrist, or other party located remotely for review.

It is further contemplated that the mobile communication device 123 can be used to train and/or guide the operator to perform eye exams and/or make assessments of the eye health of the subject whose eyes are being examined. A software application (e.g., "an app") executed by an electronic processing system (e.g., the electronic processing system of the mobile communication device 123, the electronics of handheld ophthalmic device 100 or a combination thereof) can be used to provide training and/or guide the operator. In some implementations, for example, the software application can be operated in one of the following two modes: an expert mode and a novice mode. In the expert mode, the mobile communication device 123 can be configured as a telemedicine platform that can be used by a trained ophthalmologist or optometrist to examine the eye, assess the health of the eye and/or provide treatment or clinical remedies, on-site. The novice mode is configured for use by non-professionals to perform an examination of a subject's eye. Accordingly, in the novice mode, the mobile communication device 123 can be configured to provide instructions to perform the various diagnostic tests. In the novice mode, the mobile communication device 123 can provide a self-assess decision tree to aid the non-professional to analyze the obtained images without the ophthalmologist. Furthermore, the mobile communication device 123 can be provided with telemedicine support. Thus, in case that the operator is not able to assess the injury, the operator can send the images and/or video to a remote healthcare professional, ophthalmologist, optometrist, or other healthcare provider (e.g., physician) for a diagnosis or examination advice.

Conclusion

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. No single feature or group of features is necessary or indispensable to each and every embodiment.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A handheld ophthalmic device for imaging an eye having a retina, said device comprising:
    a handheld mechanical assembly having a front side and a rear side, said front side being curved, said handheld mechanical assembly comprising:
        a first camera and a first source of illumination configured as a non-contact ophthalmoscope, said first camera configured to image the retina of the eye when spaced apart from the eye so as to provide non-contact imaging of the eye;
        a second source of illumination configured to be laterally translated along a curved track on the curved front side of said mechanical assembly;
        at least one second camera, wherein the second source of illumination and the at least one second camera are configured as a slit lamp, said second camera on said front side of said handheld mechanical assembly;
    electronics; and
    a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the docking system is configured such that the smartphone, the cellphone or the electronic tablet is disposed on the rear side of the mechanical assembly opposite the front side of the mechanical assembly through which the ophthalmoscope and the slit lamp are configured to emit and capture light;
    wherein said track is between said second camera and said second source of illumination and the distance between the second source of illumination and the second camera is less than the distance between the track and the location of the eye,
    wherein the first camera and the at least one second camera are different from a camera integrated in the smartphone, cellphone, or electronic tablet;
    wherein the handheld ophthalmic device is configured to be operated in a first mode as a non-contact ophthalmoscope and in a second mode as a slit-lamp to examine an eye of a subject facing the front side of the mechanical assembly, and
    wherein the electronics are configured to electronically communicate with the smartphone, the cellphone or the electronic tablet and transport one or more images captured by the first camera in the first mode or the at least one second camera in the second mode to the smartphone, the cellphone or the electronic tablet.

2. The handheld ophthalmic device of claim 1, further comprising the smartphone, the cellphone or the electronic tablet, wherein the smartphone, the cellphone or the electronic tablet comprises a software application which when executed by an electronic processing system guides an operator to capture the one or more images.

3. The handheld ophthalmic device of claim 1, further comprising the smartphone, the cellphone or the electronic tablet, wherein the smartphone, the cellphone or the electronic tablet comprises a software application which when executed by an electronic processing system guides an operator to perform an assessment based on the captured one or more images.

4. The handheld ophthalmic device of claim 1, further comprising the smartphone, the cellphone or the electronic tablet, wherein the one or more images captured by the first or the at least one second camera are stored in the memory device of the smartphone, the cellphone or the electronic tablet.

5. The handheld ophthalmic device of claim 1, further comprising the smartphone, the cellphone or the electronic tablet, wherein the smartphone, the cellphone or the electronic tablet comprises instructions which when executed by an electronic processing system causes the smartphone, the cellphone or the electronic tablet to transport the one or more images captured by the first or the at least one second camera to a health care professional, an ophthalmologist or an optometrist at a remote location.

6. The handheld ophthalmic device of claim 1, further comprising the smartphone, the cellphone or the electronic tablet, wherein the smartphone, the cellphone or the electronic tablet comprises instructions which when executed by an electronic processing system causes the smartphone, the cellphone or the electronic tablet to display the one or more images captured by the first or the at least one second camera on the display device of the smartphone, the cellphone or the electronic tablet.

7. The handheld ophthalmic device of claim 1, further comprising the smartphone, the cellphone or the electronic tablet, wherein the electronics is configured to electronically communicate with the smartphone, the cellphone or the electronic tablet.

8. The handheld ophthalmic device of claim 1, further comprising the smartphone, the cellphone or the electronic tablet, wherein an electronic processing system of the smartphone is configured to obtain instructions stored in a non-transitory storage medium, and wherein the obtained instructions when executed by an electronic processing system cause the smartphone, the cellphone or the electronic tablet to:
guide an operator to capture the one or more images or guide an operator to perform an assessment based on the captured one or more images.

9. The handheld ophthalmic device of claim 1, wherein the electronics comprises a transmitter and a receiver.

10. The handheld ophthalmic device of claim 1, wherein the electronics comprises a wireless transmitter and a wireless receiver.

11. The handheld ophthalmic device of claim 1, wherein the at least one second camera is part of a stereoscopic imaging system comprising a pair of cameras.

12. The handheld ophthalmic device of claim 1, wherein said handheld mechanical assembly has a length from 4 to 8 inches, a height from 2 to 5 inches and a width from 1 to 3 inches.

13. The ophthalmic device of claim 1, wherein said handheld ophthalmic device has a weight less than or equal to 3 pounds.

14. The ophthalmic device of claim 1, wherein said handheld ophthalmic device has a weight from about 1 to 1.5 lbs.

15. The handheld ophthalmic device of claim 1, further comprising a third camera and a third source of illumination configured as a near infrared pupillography instrument.

16. The handheld ophthalmic device of claim 15, wherein the third source of illumination is configured to emit near infrared light in a wavelength range between 700 nm and 1100 nm.

17. The handheld ophthalmic device of claim 15, wherein the third camera is configured to receive and detect near infrared light.

18. The handheld ophthalmic device of claim 15, wherein the third camera is configured to obtain a video of pupillary reaction of the subject's eye when illuminated by light from the third source of illumination.

19. The handheld ophthalmic device of claim 15, further comprising a fourth source configured to emit white light.

20. The handheld ophthalmic device of claim 19, wherein the third camera is configured to obtain an image of the subject's eye or face when illuminated by light from the fourth source of illumination.

21. A handheld ophthalmic device comprising:
a mechanical assembly comprising:
a mobile slit-lamp configured to be laterally translated along tracks disposed on a surface of the mechanical assembly, the mobile slit-lamp comprising a light source;
at least one camera;
electronics; and
a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the docketing system is configured such that the smartphone, the cellphone or the electronic tablet is disposed on a rear side of the mechanical assembly opposite a front side of the mechanical assembly through which the mobile slit lamp is configured to emit and capture light,
wherein the at least one camera is not integrated in the smartphone, the cellphone or the electronic tablet, wherein the electronics is configured to transport one or more images captured by the imaging system to the smartphone, the cellphone or the electronic tablet, and
wherein said light source of said mobile slit-lamp is configured to cross in front of said at least one camera at at least one point when translated along said tracks such that said mobile slit-lamp obstructs the field of view of the at least one camera.

22. The handheld ophthalmic device of claim 21, wherein the at least one camera is part of a stereoscopic imaging system comprising a pair of cameras.

23. The handheld ophthalmic device of claim 21, wherein said mechanical assembly has a length from 4 to 8 inches, a height from 2 to 5 inches and a width from 1 to 3 inches.

24. The ophthalmic device of claim 21, wherein said handheld ophthalmic device has a weight less than or equal to 3 pounds.

25. The ophthalmic device of claim 21, wherein said handheld ophthalmic device has a weight from about 1 to 1.5 lbs.

26. The handheld ophthalmic device of claim 21, wherein the assembly further comprises:
a camera configured to detect infrared light and a source of infrared illumination,
wherein the source of infrared illumination is configured to emit near infrared light in a wavelength range between 700 nm and 1100 nm, and
wherein the camera configured to detect infrared light is configured to receive and detect near infrared light.

27. The handheld ophthalmic device of claim 26, wherein the camera configured to detect infrared light is configured to obtain a video of pupillary reaction of a subject's eye when illuminated by light from the source of infrared illumination.

28. The handheld ophthalmic device of claim 27, wherein the camera configured to detect infrared light is configured to obtain an image of a subject's eye or face when illuminated by light from an additional source of illumination.

29. A handheld ophthalmic device for imaging an eye having a retina, said device comprising:
a handheld mechanical assembly having a front side and a rear side, said handheld mechanical assembly comprising:
a first camera and a first source of illumination configured as a non-contact ophthalmoscope, said first camera configured to image the retina of the eye when spaced apart from the eye so as to provide non-contact imaging of the eye;
a second source of illumination, the second source of illumination configured to emit light in a wavelength range between about 700 nm and about 1100 nm;
a second camera configured to receive and detect light in a wavelength range between about 700 nm and about 1100 nm;
electronics; and
a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the docketing system is configured such that the smartphone, the cellphone or the electronic tablet is disposed on the rear side of the mechanical assembly opposite the front side of the mechanical assembly through which the first and second source of illumination are configured to emit light, wherein the mechanical assembly comprises at least one third camera configured to image an eye of a subject illuminated by light from a third source of illumination, wherein the third source of illumination and the at least one third camera are configured as a slit lamp, wherein said third source of illumination is configured to be translated along a curved track on said front side of said mechanical assembly, wherein said curved track is between said third camera and said third source of illumination, wherein said curved track has a radius of curvature larger than the distance between said front side and said rear side of said handheld mechanical assembly, and wherein said third camera is not part of the smartphone, the cellphone or the electronic tablet.

wherein the first camera and the second camera are not part of the smartphone, the cellphone or the electronic tablet, and wherein the electronics is configured to transport one or more images captured by the first or the second camera to the smartphone, the cellphone or the electronic tablet.

30. The handheld ophthalmic device of claim 29, wherein the second camera is configured to obtain a video of pupillary reaction of a subject's eye when illuminated by light from the second source of illumination.

31. The handheld ophthalmic device of claim 29, wherein the second camera is configured to obtain an image of a subject's eye or face when illuminated by light from another source of illumination.

32. The handheld ophthalmic device of claim 29, wherein said handheld mechanical assembly has a length from 4 to 8 inches, a height from 2 to 5 inches and a width from 1 to 3 inches.

33. An ophthalmic device for imaging an eye having a retina, said device comprising:
  a stand; and
  a handheld mechanical assembly having a front side and a rear side, said handheld mechanical assembly configured to be removably attached to the stand, wherein the handheld mechanical assembly comprises:
    a first camera and a first source of illumination configured as a non-contact ophthalmoscope, said first camera configured to image the retina of the eye when spaced apart from the eye so as to provide non-contact imaging of the eye;
    electronics; and
    a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the docketing system is configured such that the smartphone, the cellphone or the electronic tablet is disposed on the rear side of the mechanical assembly opposite the front side of the mechanical assembly through which the ophthalmoscope is configured to emit and capture light,
    at least one second camera that is not part of the smartphone, the cellphone or the electronic tablet; and
    a second source of illumination configured to be laterally translated along a curved track, the second source of illumination and said at least one second camera being configured as a slit lamp,
    wherein said curved track is between said at least one second camera and said second source of illumination,
    wherein said curved track has a radius of curvature larger than the distance between said front side and said rear side of said handheld mechanical assembly,
    wherein the first camera is not part of the smartphone, the cellphone or the electronic tablet,
    wherein said at least one second camera is not part of the smartphone, the cellphone or the electronic tablet,
    wherein the electronics is configured to transport one or more images captured by the first camera to the smartphone, the cellphone or the electronic tablet.

34. The ophthalmic device of claim 33, wherein the stand is portable.

35. The ophthalmic device of claim 33, wherein the stand comprises a chinrest.

36. The ophthalmic device of claim 33, wherein the second camera is configured to obtain an image of the subject's eye or face.

37. The ophthalmic device of claim 33, wherein said handheld mechanical assembly has a length from 4 to 8 inches, a height from 2 to 5 inches and a width from 1 to 3 inches.

38. The ophthalmic device of claim 33, further comprising a camera configured to receive and detect near infrared light.

39. The ophthalmic device of claim 38, wherein the camera configured to receive and detect near infrared light is configured to obtain a video of pupillary reaction of the subject's eye when illuminated by light from a source of infrared illumination.

40. An ophthalmic device comprising:
  a stand; and
  a handheld ophthalmic device configured to be removably attached to the stand, the handheld ophthalmic device comprising:
    a source of illumination configured to be laterally translated along a curved surface of the handheld ophthalmic device;
    at least one camera;
    electronics; and
    a docking system configured to receive and hold a smartphone, a cellphone or an electronic tablet, wherein the smartphone, the cellphone or the electronic tablet comprises a display device, a memory device, and a mobile communication system configured to communicate over a distance greater than about 1000 feet, wherein the docketing system is configured such that the smartphone, the cellphone or the electronic tablet is disposed on the rear side of the mechanical assembly opposite the front side of the mechanical assembly through which the source of illumination is configured to emit light,
    wherein said curved surface is between said at least one camera and said source of illumination and the distance between the source of illumination and the at least one camera is less than the distance between the curved surface and the location of the eye.
    wherein the at least one camera is not part of the smartphone, the cellphone or the electronic tablet, and wherein the electronics is configured to electronically communicate with the smartphone, the cellphone or the electronic tablet.

41. The ophthalmic device of claim 40, wherein the at least one camera is configured to capture one or more images of a subject's eye when illuminated by light from the source of illumination.

42. The ophthalmic device of claim 40, wherein the wherein the stand is portable.

43. The ophthalmic device of claim 40, wherein the stand comprises a chinrest.

44. The ophthalmic device of claim 40, wherein said illumination source is configured as a slit lamp.

\* \* \* \* \*

UNITED STATES PATENT AND TRADEMARK OFFICE
CERTIFICATE OF CORRECTION

PATENT NO. : 11,730,356 B2
APPLICATION NO. : 15/806279
DATED : August 22, 2023
INVENTOR(S) : Michael P. Browne et al.

It is certified that error appears in the above-identified patent and that said Letters Patent is hereby corrected as shown below:

On the Title Page

On Page 2, Column 2, Line 21, under item (56) Other Publications, delete "-prited-" and insert -- -printed- --.

On Page 2, Column 2, Line 23, under item (56) Other Publications, delete "erasure" and insert --ensure--.

On Page 2, Column 2, Line 28, under item (56) Other Publications, delete "ocula" and insert --ocular--.

On Page 2, Column 2, Line 44, under item (56) Other Publications, delete "devensemedianetwork" and insert --defensemedianetwork--.

In the Specification

In Column 3, Line 62, delete "opthalmoscope" and insert --ophthalmoscope--.

In Column 8, Line 25, delete "camera;" and insert --camera.--.

In Column 13, Line 13, delete "designes," and insert --designs,--.

In the Claims

In Column 29, Claim 14, Line 24, delete "from about" and insert --from--.

In Column 29, Claim 21, Line 60, delete "docketing" and insert --docking--.

In Column 30, Claim 25, Line 20, delete "from about" and insert --from--.

Signed and Sealed this
Third Day of September, 2024

Katherine Kelly Vidal
*Director of the United States Patent and Trademark Office*

CERTIFICATE OF CORRECTION (continued)
U.S. Pat. No. 11,730,356 B2

In Column 30, Claim 29, Line 64, delete "docketing" and insert --docking--.

In Column 31, Claim 29, Line 20, delete "tablet." and insert --tablet,--.

In Column 31, Claim 33, Line 59, delete "docketing" and insert --docking--.

In Column 32, Claim 40, Line 55, delete "docketing" and insert --docking--.

In Column 32, Claim 40, Line 65, delete "eye." and insert --eye,--.

In Column 33, Claim 42, Lines 8-9, delete "wherein the wherein the" and insert --wherein the--.